US006897052B1

(12) United States Patent
Korczak et al.

(10) Patent No.: US 6,897,052 B1
(45) Date of Patent: May 24, 2005

(54) N-ACETYLGLYCOSAMINYL TRANSFERASE GENES

(75) Inventors: Bozena Korczak, Toronto (CA); April Lew, Toronto (CA)

(73) Assignee: GlycoDesign Holdings Ltd., Richmond (CA)

( * ) Notice: Subject to any disclaimer, the term of this patent is extended or adjusted under 35 U.S.C. 154(b) by 0 days.

(21) Appl. No.: 09/762,569

(22) PCT Filed: Aug. 5, 1999

(86) PCT No.: PCT/CA99/00711

§ 371 (c)(1),
(2), (4) Date: Apr. 27, 2001

(87) PCT Pub. No.: WO00/08171

PCT Pub. Date: Feb. 17, 2000

Related U.S. Application Data
(60) Provisional application No. 60/095,919, filed on Aug. 7, 1998.

(51) Int. Cl.[7] .......................... C12P 21/06; C12N 9/00; C12N 9/10; C12N 1/20; C12N 15/00; C07H 21/04
(52) U.S. Cl. ...................... 435/193; 435/69.1; 435/183; 435/200; 435/252.3; 435/320.1; 435/325; 435/530; 435/350; 435/536; 435/23.2; 435/23.4; 435/23.5; 435/233.5; 435/24.31; 435/24.33
(58) Field of Search ............................... 435/69.1, 183, 435/193, 200, 252.3, 320.1; 530/350; 536/23.2, 23.4, 23.5, 24.31, 24.33

(56) References Cited

U.S. PATENT DOCUMENTS

| | | | |
|---|---|---|---|
| 5,032,505 A | 7/1991 | Pierce et al. | |
| 5,602,003 A | 2/1997 | Pierce et al. | |
| 5,705,367 A | 1/1998 | Gotschlich | |
| 5,707,846 A | 1/1998 | Taniguchi et al. | |
| 5,780,603 A | 7/1998 | Hindsgaul | |
| 5,834,284 A | 11/1998 | Taniguchi et al. | |
| 6,015,701 A | 1/2000 | Pierce et al. | |

FOREIGN PATENT DOCUMENTS

EP  585 109 A2 * 3/1994
WO  WO 94/00475  1/1994

OTHER PUBLICATIONS

Evans et al., "HGTD submission," XP002120235, nucleotides 57575 to 58705, Oct. 31, 1997.
Saito et al., "cDNA cloning and chromosomal mapping of human N–acetylgucosaminyltransferase V," Biochemical and Biophysical Research Communications, vol. 198, No. 1, pp. 318–327 (1994).

Hillier et al., "The WashU–Merck EST Project," XP002119781, Oct. 10, 1995.
Schachter, H., Biochem. Cell. Biol., 64: 163–181, 1986.
van den Eijnden, D. H. et al., 263:12461–12465, 1988.
Yousefi, S. et al., J. Biol. Chem., 266: 1772–1783, 1991.
Heffernan, M. et al., J. biol. Chem., 268: 1242–1251, 1993.
Shoreibah, M. et al., J. Biol., 268: 15381–15385, 1993.
Saito et al., Eur. J. Biochem., 233: 18–26, 1995.
Buckhaults, P., J. Biol. Chem., 272: 19575–19581, 1997.
Yamashita, K. et al., J. Biol. Chem., 260: 3963–3969, 1985.
Pierce, M. and Arango, J., J. Biol. Chem., 261: 10772–10777, 1986.
Dennis, J. et al., Science, 236: 582–585, 1987.
Guilloux, Y. et al (1996) J. Exp. Med. 183:1173–1183.
Miyoshi, e. et al, (1993) Cancer Res. 53: 3899–3902, 1993.
Demetriou, M. et al (1995) J. Cell Biol. 130:383.
Lu, Y. et al (1994) Clin. Exp. Metastasis 12:47–54.
Chirgwin, J. et al., Biochemistry, 18: 5294–5299, 1979.
Carillo, H. and Lipman, D., Siam J., Applied Math, 48: 1073, 1988.
Devereux, J. et al., Nucleic Acids Research, 12 (1): 387–395, 1984.
Atschul, S.F. et al., J. Molec. Biol., 215: 403, 1990.
Dayhoff, M. et al., Methods in Enzymology, 91: 524–545, (1983).
Korczak, B. et al; Glycobiology Vol 10, pp. 595–599, 2000.
Hammer, R., et al., Nature, 315: 680–683, 1985.
Palmiter, R., et al., Science, 222: 809–814, 1983.
Brinster, R., et al., Proc. Natl. Acad. Sci. USA, 82: 4438–4442, 1985.
Palmiter, R amd Brinster R., Cell, 41: 343–345, 1985.
Lasko, M. et al., Proc. Nat'l Acad. Sci. USA, 89: 6232–6236, 1992.
Gu, H. et al., Science, 265: 103–106, 1994.
Merrifield, R., J. Am. Assoc., 85:2149–2154, 1964.
Koenderman, A. et al., FEBS Lett., 222: 42–46.
Palcic, M. et al., Glycoconjugate, 5: 49–63, 1988.
Pierce, M., et al., Biochem. Biophys, Res. Comm., 146: 679–684, 1987.
Gee, J.E. et al., In: Huber, B.E. amd B.I. Carr, Molecular Immunologic Approaches, Futura Publishing Co., Mt. Kisco, N.Y., 1994.
Current Protocols in Molecular Biology, John Wiley & Sons, N.Y. (1989), 6.3.1–6.3.6.
Fernandes, B. et al., Cancer Research, 51:718–723, 1991.

* cited by examiner

*Primary Examiner*—Manjunath Rao
(74) *Attorney, Agent, or Firm*—Merchant & Gould, P.C.

(57) ABSTRACT

N-acetylglycosaminyltransferase V nucleic acids, proteins encoded by the nucleic acids, and uses of the nucleic acids and proteins.

10 Claims, 3 Drawing Sheets

Expression of GNTV and GNTV-b in different tumor types

N-ACETYLGLYCOSAMINYL TRANSFERASE GENES

This application claims the benefit of Provisional Application No. 60/095,919, filed Aug. 7, 1998.

FIELD OF THE INVENTION

The invention relates to novel N-acetylglycosaminyltransferase V nucleic acids, proteins encoded by the nucleic acids, and uses of the nucleic acids and proteins.

BACKGROUND OF THE INVENTION

Protein glycosylation is mediated by a series of enzymes found in the Golgi apparatus. Many of the enzymes in this pathway are subject to regulation during embryogenesis, lymphocyte activation, and in cancer progression. Structural diversity of carbohydrates on cell surfaces and secreted or non-secreted (e.g. receptors) proteins affects their function and the associated cell biology. Somatic mutations and drugs which block the biosynthesis of -GlcNAcβ1-6Manβ-branching of N-linked oligosaccharides, also inhibit organ colonisation, invasion in vitro, and limit solid tumor growth in vivo.

Synthesis of GlcNAc-branched carbohydrate structure is dependent upon N-acetylglycosaminyltransferases, one of which is N-acetylglycosaminyltransferase V (GlcNAc-TV). GlcNAc-TV catalyzes the addition of 1-6GlcNAc to thetrimannosyl core in the biosynthetic pathway for branched complex-type N-linked oligosaccharides found on some cell surface and secreted glycoproteins (Schachter, H. (1986) Biochem. Cell. Biol. 64: 163–181). The 1-6GlcNAc product of GlcNAc-TV is the preferred antenna and rate limiting substrate in the pathway for addition of terminal polylactosamine sequences which affect cell-cell and cell-substratum interactions (van den Eijnden, D. H. et al, (1988) 263:12461–12465; Yousefi, S. et al, (1991) J. Biol Chem. 266:1772–1783; and Heffernan, M. et al, (1993) J. Biol. Chem. 268:1242–1251).

The rat (Shoreibah, M. et al (1993), 268:15381–15385) and human (Saito, H. et al. (1994), Biochem. Biophys. Res. Commun. 198:318–327 233:18–26) GlcNAc-TV sequences predict a 741 amino acid type II glycoprotein. The human GlcNAc-TV gene is located on human chromosome 2q21 with 17 exons and spans 155Kb (Saito et al., (1995) Eur. J. Biochem. 233: 18–26). The putative promoter region of the GlcNAc-TV gene has AP1 and PEA3/ets binding sites, and is responsive to ras signaling pathways (Buckhaults P J Biol Chem (1997) 272:19575–19581).

Oncogenic transformation of rodent fibroblasts by polyoma virus, v-src, H-ras or v-fps leads to increased GlcNAc-TV expression (Yamashita, K. et al, (1985) J. Biol. Chem. 260:3963–3969; Pierce, M and Arango, J. (1986) J. Biol. Chem. 261: 10772–10777, Dennis, J et al. (1987) Science 236::582–585, 1987), and in human carcinomas of breast, colon and skin GlcNAcTV-generated structures correlate with pathological staging of tumors (Fernandes, B. et al (1991) 51:718–723). The GlcNAc-TV message is also subject to increased frequency of alternate splicing in tumors cells, resulting in a peptide encoded by an intron sequence of the GlcNAc-TV gene which has been identified as a widely occurring "tumor-associated antigen". Fifty percent of tested human melanoma tumors expressed this antigen, while it is absent in normal tissues (Guilloux, Y. et al (1996) J. Exp. Med. 183:1173–1183). In a rat model of heritable liver cancer, GlcNAc-TV transcript levels are elevated in primary tumors and lymph node metastases (Miyoshi, e. et al, (1993) Cancer Res. 53:3899–3902, 1993). In addition, topical expression of GlcNAc-TV in epithelial cells results in morphological transformation and tumorogenesis (Demetriou, M. et al (1995) J. Cell Biol. 130:383), while tumor cell mutants selected for loss of GlcNAc-TV activity show reduced malignant potential in vivo (Lu, Y. et al (1994) Clin. Exp. Metastasis 12:47–54).

SUMMARY OF THE INVENTION

The present inventors have identified novel GlcNAc-TV nucleic acid molecules. The nucleic acids are herein designated "glcNAc-TV-b" or "GlcNAc-TV-b nucleic acid molecule" and "glcNAc-TV-c" or "GlcNAc-TV-c nucleic acid molecule". The proteins encoded by the nucleic acid molecules are herein designated "GlcNAc-TV-b" or "GlcNAc-TV-b Protein", and "GlcNAc-TV-c" or "GlcNAc-TV-c Protein".

Broadly stated the present invention contemplates an isolated nucleic acid molecule encoding a protein of the invention, including mRNAs, DNAs, cDNAs, genomic DNAs, PNAs, as well as antisense analogs and biologically, diagnostically, prophylactically, clinically or therapeutically useful variants or fragments thereof, and compositions comprising same.

In particular, the present invention contemplates an isolated GlcNAc-TV-b or GlcNAc-TV-c nucleic acid molecule comprising a sequence that comprises at least 18 nucleotides and hybridizes under stringent conditions to the complementary nucleic acid sequence of SEQ. ID. NO. 1, or a degenerate form thereof. Further embodiments of this aspect of the invention provide biologically, diagnostically, prophylactically, clinically or therapeutically useful variants thereof and compositions comprising same.

The invention also contemplates an isolated GlcNAc-TV-b or GlcNAc-TV-c protein encoded by a nucleic acid molecule of the invention, a truncation, an analog, an allelic or species variation thereof, or a homolog of a protein of the invention, or a truncation thereof. (Truncations, analogs, allelic or species variations, and homologs are collectively referred to herein as "GlcNAc-TV-b Related Proteins" or "GlcNAc-TV-c Related Proteins).

The nucleic acid molecules of the invention permit identification of untranslated nucleic acid sequences or regulatory sequences which specifically promote expression of genes operatively linked to the promoter regions. Identification and use of such promoter sequences are particularly desirable in instances, such as gene transfer or gene therapy, which can specifically require heterologous gene expression in a limited environment (e.g. CNS environment). The invention therefore contemplates a nucleic acid encoding a regulatory sequence of a nucleic acid molecule of the invention such as a promoter sequence, preferably a regulatory sequence of glcNAc-TV-b or glcNAc-TV-c.

The nucleic acid molecules which encode for a mature GlcNAc-TV-b or GlcNAc-TV-c protein may include only the coding sequence for the mature polypeptide (SEQ ID NO. 5 or 9); the coding sequence for the mature polypeptide and additional coding sequences (e.g. leader or secretory sequences, proprotein sequences); the coding sequence for the mature polypeptide (and optionally additional coding sequence) and non-coding sequence, such as introns or non-coding sequences 5' and/or 3' of the coding sequence of the mature polypeptide (e.g. SEQ ID NO. 3).

Therefore, the term "nucleic acid molecule encoding a protein" encompasses a nucleic acid molecule which includes only coding sequence for the protein as well as a nucleic acid molecule which includes additional coding and/or non-coding sequences.

The nucleic acids of the invention may be inserted into an appropriate expression vector, and the vector may contain the necessary elements for the transcription and translation of an inserted coding sequence. Accordingly, recombinant expression vectors may be constructed which comprise a nucleic acid molecule of the invention, and where appropriate one or more transcription and translation elements linked to the nucleic acid molecule.

Vectors are contemplated within the scope of the invention which comprise regulatory sequences of the invention, as well as chimeric gene constructs wherein a regulatory sequence of the invention is operably linked to a nucleic acid sequence encoding a heterologous protein (i.e. a protein not naturally expressed in the host cell), and a transcription termination signal.

A recombinant expression vector can be used to transform host cells to express a GlcNAc-TV-b Protein, GlcNAc-TV-b Related Proteins, a GlcNAc-TV-c Protein, or GlcNAc-TV-c Related Proteins, or a heterologous protein. Therefore, the invention further provides host cells containing a recombinant molecule of the invention. The invention also contemplates transgenic non-human mammals whose germ cells and somatic cells contain a recombinant molecule comprising a nucleic acid molecule of the invention in particular one that encodes an analog of GlcNAc-TV-b or GlcNAc-TV-c, or a truncation of GlcNAc-TV-b or GlcNAc-TV-c.

The proteins of the invention may be obtained as an isolate from natural cell sources, but they are preferably produced by recombinant procedures. In one aspect the invention provides a method for preparing a GlcNAc-TV-b Protein, a GlcNAc-TV-b Related Protein, a GlcNAc-TV-c Protein, or a GlcNAc-TV-c Related Protein utilizing the purified and isolated nucleic acid molecules of the invention. In an embodiment a method for preparing a GlcNAc-TV-b Protein, a GlcNAc-TV-b Related Protein, a GlcNAc-TV-c Protein, or a GlcNAc-TV-c Related Protein is provided comprising:
  (a) transferring a recombinant expression vector of the invention having a nucleotide sequence encoding a GlcNAc-TV-b Protein, a GlcNAc-TV-b Related Protein, a GlcNAc-TV-c Protein, or a GlcNAc-TV-c Related Protein, into a host cell;
  (b) selecting transformed host cells from untransformed host cells;
  (c) culturing a selected transformed host cell under conditions which allow expression of the GlcNAc-TV-b Protein, GlcNAc-TV-b Related Protein, GlcNAc-TV-c Protein, or GlcNAc-TV-c Related Protein; and
  (d) isolating the GlcNAc-TV-b Protein, GlcNAc-TV-b Related Protein, GlcNAc-TV-c Protein, or GlcNAc-TV-c Related Protein.

The invention further broadly contemplates a recombinant GlcNAc-TV-b Protein, GlcNAc-TV-b Related Protein, GlcNAc-TV-c Protein, or GlcNAc-TV-c Related Protein obtained using a method of the invention.

A GlcNAc-TV-b Protein, a GlcNAc-TV-b Related Protein, a GlcNAc-TV-c Protein, or a GlcNAc-TV-c Related Protein of the invention may be conjugated with other molecules, such as proteins, to prepare fusion proteins or chimeric proteins. This may be accomplished, for example, by the synthesis of N-terminal or C-terminal fusion proteins.

The invention further contemplates antibodies having specificity against an epitope of a GlcNAc-TV-b Protein, a GlcNAc-TV-b Related Protein, a GlcNAc-TV-c Protein, or a GlcNAc-TV-c Related Protein of the invention. Antibodies may be labeled with a detectable substance and used to detect proteins of the invention in biological samples, tissues, and cells.

The invention also permits the construction of nucleotide probes which are unique to the nucleic acid molecules of the invention or to proteins of the invention. Therefore, the invention also relates to a probe comprising a sequence encoding a protein of the invention, or a part thereof. The probe may be labeled, for example, with a detectable substance and it may be used to select from a mixture of nucleotide sequences a nucleic acid molecule of the invention including nucleic acid molecules coding for a protein which displays one or more of the properties of a protein of the invention.

In accordance with an aspect of the invention there is provided a method of, and products for, diagnosing and monitoring conditions mediated by a GlcNAc-TV-b Protein, a GlcNAc-TV-b Related Protein, a GlcNAc-TV-c Protein, or a GlcNAc-TV-c Related Protein by determining the presence of nucleic acid molecules and proteins of the invention.

Still further the invention provides a method for evaluating a test compound for its ability to modulate the biological activity of a GlcNAc-TV-b Protein, a GlcNAc-TV-b Related Protein, a GlcNAc-TV-c Protein, or a GlcNAc-TV-c Related Protein of the invention. For example a substance which inhibits or enhances the catalytic activity of a GlcNAc-TV-b Protein, a GlcNAc-TV-b Related Protein, a GlcNAc-TV-c Protein, or a GlcNAc-TV-c Related Protein may be evaluated. "Modulate" refers to a change or an alteration in the biological activity of a protein of the invention. Modulation may be an increase or a decrease in activity, a change in characteristics, or any other change in the biological, functional, or immunological properties of the protein.

Compounds which modulate the biological activity of a protein of the invention may also be identified using the methods of the invention by comparing the pattern and level of expression of a nucleic acid molecule or protein of the invention in tissues and cells, in the presence, and in the absence of the compounds.

Methods are also contemplated that identify compounds or substances (e.g. proteins) which bind to glcNAc-TV-b or glcNAc-TV-c regulatory sequences (e.g. promoter sequences, enhancer sequences, negative modulator sequences).

The substances and compounds identified using the methods of the invention may be used to modulate the biological activity of a GlcNAc-TV-b Protein, a GlcNAc-TV-b Related Protein, a GlcNAc-TV-c Protein, or a GlcNAc-TV-c Related Protein of the invention, and they may be used in the treatment of conditions mediated by the proteins including but not limited to proliferative diseases such as cancer, viral, bacterial, and parasitic infections, to stimulate hematopoietic progenitor cell growth, or confer protection against chemotherapy or radiation therapy. Accordingly, the nucleic acid molecules and proteins of the invention, and substances and compounds may be formulated into compositions for administration to individuals suffering from one or more of these conditions. Therefore, the present invention also relates to a composition comprising one or more of a nucleic acid molecule or protein of the invention, or a substance or compound identified using the methods of the invention, and a pharmaceutically acceptable carrier, excipient or diluent. A method for treating or preventing these conditions is also provided comprising administering to a patient in need thereof, a composition of the invention.

The present invention provides the means necessary for production of gene-based therapies directed at the brain. These therapeutic agents may take the from of polynucleotides comprising all or a portion of a nucleic acid of the invention comprising a regulatory sequence of glcNAc-TV-b or glcNAc-TV-c placed in appropriate vectors or delivered to target cells in more direct ways.

Having provided novel GlcNAc TV proteins, and nucleic acids encoding same, the invention accordingly further provides methods for preparing oligosaccharides e.g. two or more saccharides. In specific embodiments, the invention relates to a method for preparing an oligosaccharide comprising contacting a reaction mixture comprising an activated GlcNAc, and an acceptor in the presence of a GlcNAc-TV-b Protein, a GlcNAc-TV-b Related Protein, a GlcNAc-TV-c Protein, or a GlcNAc-TV-c Related Protein of the invention.

In accordance with a further aspect of the invention, there are provided processes for utilizing proteins or nucleic acid molecules of the invention, for in vitro purposes related to scientific research, synthesis of DNA, and manufacture of vectors.

These and other aspects, features, and advantages of the present invention should be apparent to those skilled in the art from the following drawings and detailed description.

DESCRIPTION OF THE DRAWINGS

The invention will be better understood with reference to the drawings in which.

DETAILED DESCRIPTION OF THE INVENTION

Figure 1:
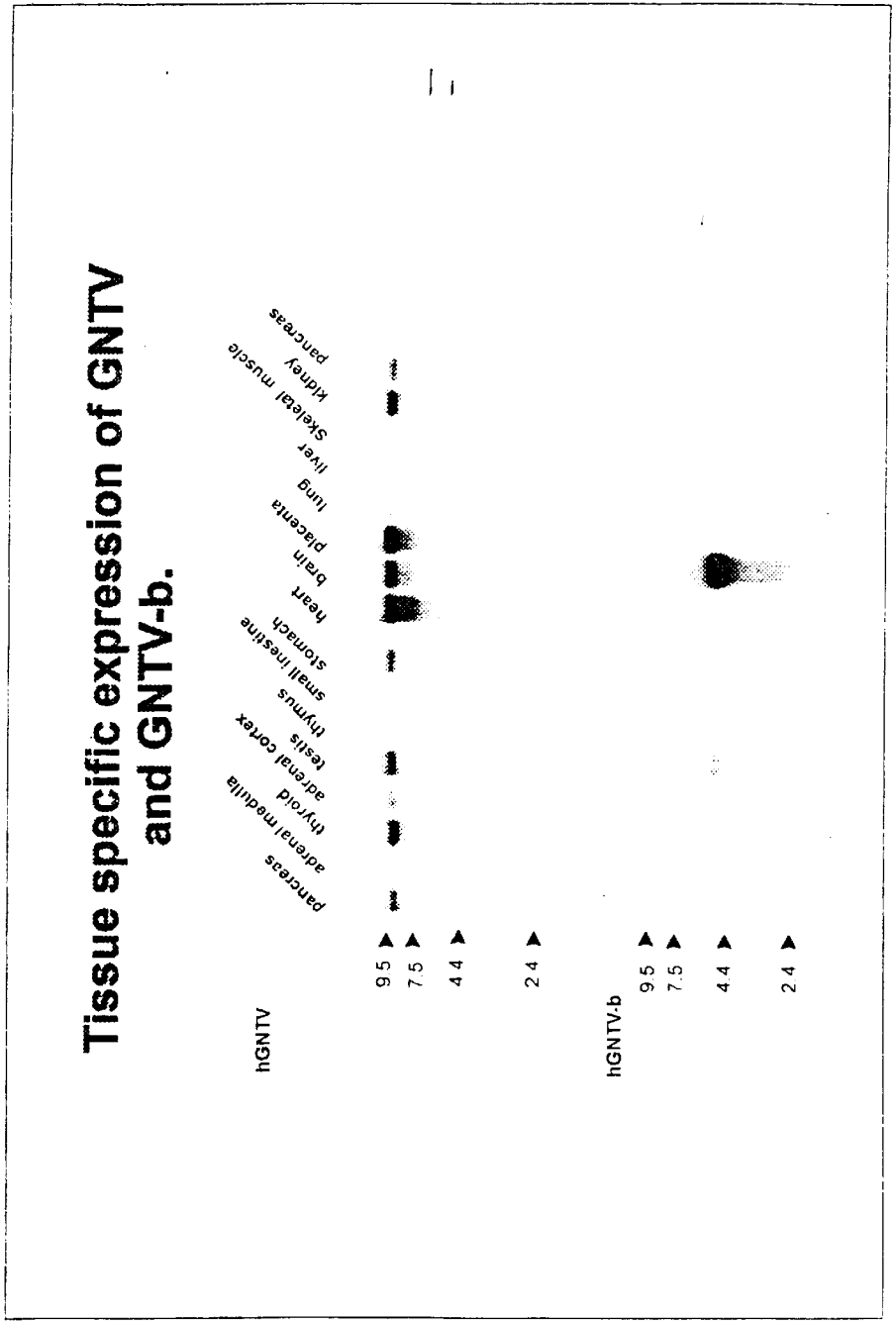
FIG. 1 is a reproduction of autoradiograms resulting from a Northern hydridization experiment in which mRNA isolated from different human tissues was sized-fractionated and probed with radioactive human partial GlcNAc-TV clone (nucleotides 1508–1921) and human partial GlcNAc-TV-b (nucleotides 1959–2417)

In accordance with the present invention there may be employed conventional molecular biology, microbiology, and recombinant DNA techniques within the skill of the art. Such techniques are explained fully in the literature. See for example, Sambrook, Fritsch, & Maniatis, Molecular Cloning: A Laboratory Manual, Second Edition (1989) Cold Spring Harbor Laboratory Press, Cold Spring Harbor, N.Y.); DNA Cloning: A Practical Approach. Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. I. Freshney, ed. (1986) ; Immobilized Cells and enzymes IRL Press, (1986); and B. Perbal, A Practical Guide to Molecular Cloning (1984).

Nucleic Acid Molecules of the Invention

As hereinbefore mentioned, the invention provides isolated GlcNAc-TV-b and GlcNAc-TV-c nucleic acid molecules. The GlcNAc-TV-b and GlcNAc-TV-c nucleic acid molecules differ in their 3' ends.

The term "isolated" refers to a nucleic acid (or protein) removed from its natural environment, purified or separated, or substantially free of cellular material or culture medium when produced by recombinant DNA techniques, or chemical reactants, or other chemicals when chemically synthesized. Preferably, an isolated nucleic acid molecule is at least 60% free, more preferably at least 75% free, and most preferably at least 90% free from other components with which they are naturally associated. The term "nucleic acid" is intended to include modified or unmodified DNA, RNA, including mRNAs, DNAs, cDNAs, and genomic DNAs, or a mixed polymer, and can be either single-stranded, double-stranded or triple-stranded. For example, a nucleic acid sequence may be a single-stranded or double-stranded DNA, DNA that is a mixture of single-and double-stranded regions, or single-, double- and triple-stranded regions, single- and double-stranded RNA, RNA that may be single-stranded, or more typically, double-stranded, or triple-stranded, or a mixture of regions comprising RNA or DNA, or both RNA and DNA. The strands in such regions may be from the same molecule or from different molecules. The DNAs or RNAs may contain one or more modified bases. For example, the DNAs or RNAs may have backbones modified for stability or for other reasons. A nucleic acid sequence includes an oligonucleotide, nucleotide, or polynucleotide. The term "nucleic acid molecule" and in particular DNA or RNA, refers only to the primary and secondary structure and it does not limit it to any particular tertiary forms.

In an embodiment of the invention an isolated nucleic acid is contemplated which comprises:

(i) a nucleic acid sequence encoding a protein having substantial sequence identity preferably at least 70%, more preferably at least 75% sequence identity, with an amino acid sequence of SEQ. ID. NO. 2, 4, 6, 10, or 12;

(ii) nucleic acid sequences complementary to (i);

(iii) nucleic acid sequences differing from any of the nucleic acids of (i) or (ii) in codon sequences due to the degeneracy of the genetic code;

(iv) a nucleic acid sequence comprising at least 18 nucleotides and capable of hybridizing under stringent conditions to a nucleic acid sequence of SEQ. ID. NO. 1, 3, 5, 9, or 11 or to a degenerate form thereof;

(v) a nucleic acid sequence encoding a truncation, an analog, an allelic or species variation of a protein comprising an amino acid sequence of SEQ. ID. NO. 2, 4, 6, 10, or 12; or (vi) a fragment, or allelic or species variation of (i), (ii) or (iii)

In a specific embodiment, the isolated nucleic acid comprises:

(i) a nucleic acid sequence having substantial sequence identity preferably at least 70%, more preferably at least 75% sequence identity with a nucleotide sequence of SEQ. ID. NO. 1, 3, 5, 9, or 11;

(ii) nucleic acid sequences complementary to (i), preferably complementary to a full nucleic acid sequence of SEQ. ID. NO. 1, 3, 5, 9, or 11;

(iii) nucleic acid sequences differing from any of the nucleic acids of (i) to (ii) in codon sequences due to the degeneracy of the genetic code; or (iv) a fragment, or allelic or species variation of (i), (ii) or (iii).

The term "complementary" refers to the natural binding of nucleic acid molecules under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules.

In a preferred embodiment the isolated nucleic acid comprises a nucleic acid sequence encoded by an amino acid sequence of SEQ. ID. NO. 2, 4, 6, 10, or 12 or comprises a nucleotide sequence of SEQ. ID. NO. 1, 3, 5, 9, or 11 wherein T can also be U.

The terms "sequence similarity" or "sequence identity" refers to the relationship between two or more amino acid or nucleic acid sequences, determined by comparing the sequences, which relationship is generally known as "homology". Identity in the art also means the degree of sequence relatedness between amino acid or nucleic acid sequences, as the case may be, as determined by the match between strings of such sequences. Both identity and similarity can be readily calculated (Computational Molecular Biology, Lesk, A. M., ed., Oxford University Press New York, 1988; Biocomputing: Informatics and Genome Projects, Smith, D. W. ed., Academic Press, New York, 1993; Computer Analysis of Sequence Data, Part I, Griffin, A. M., and Griffin, H. G. eds. Human Press, New Jersey, 1994; Sequence Analysis in Molecular Biology, von Heinje, G., Academic Press, New York, 1987; and Sequence Analysis Primer, Gribskov, M. and Devereux, J., eds. M. Stockton Press, New York, 1991). While there are a number of existing methods to measure identity and similarity between two amino acid sequences or two nucleic acid sequences, both terms are well known to the skilled artisan (Sequence Analysis in Molecular Biology, von Heinje, G., Academic Press, New York, 1987; Sequence Analysis Primer, Gribskov, M. and Devereux, J., eds. M. Stockton Press, New York, 1991; and Carillo, H., and Lipman, D. SIAM J. Applied Math., 48:1073, 1988). Preferred methods for determining identity are designed to give the largest match between the sequences tested. Methods to determine identity are codified in computer programs. Preferred computer program methods for determining identity and similarity between two sequences include but are not limited to the GCG program package (Devereux, J. et al, Nucleic Acids Research 12(1): 387, 1984), BLASTP, BLASTN, and FASTA (Atschul, S. F. et al., J. Molec. Biol. 215:403, 1990). Identity or similarity may also be determined using the alignment algorithm of Dayhoff et al; Methods in Enzymology 91: 524–545 (1983).

Preferably, a nucleic acid molecule of the present invention has substantial sequence identity using the preferred computer programs cited herein, for example at least 70%, more preferably at least 75% nucleic acid identity; still more preferably at least 80% nucleic acid identity; and most preferably at least 90% to 95% sequence identity to a sequence of SEQ. ID. NO. 1, 3, 5, 9, or 11.

Isolated nucleic acid molecules encoding a GlcNAc-TV-b Protein or GlcNAc-TV-c Protein, and having a sequence which differs from a nucleic acid sequence of SEQ. ID. NO. 1, 3, 5, 9, or 11, due to degeneracy in the genetic code are also within the scope of the invention. Such nucleic acid molecules encode equivalent proteins but differ in sequence from a sequence of SEQ. ID. NO. 1, 3, 5, 9, or 11 due to degeneracy in the genetic code. As one example, DNA sequence polymorphisms within glcNAc-TV-b or glcNAc-TV-c may result in silent mutations which do not affect the amino acid sequence. Variations in one or more nucleotides may exist among individuals within a population due to natural allelic variation. Any and all such nucleic acid variations are within the scope of the invention. DNA sequence polymorphisms may also occur which lead to changes in the amino acid sequence of GlcNAc-TV-b Protein or GlcNAc-TV-c Protein. These amino acid polymorphisms are also within the scope of the present invention. In addition, species variations i.e. variations in nucleotide sequence naturally occurring among different species, are within the scope of the invention.

Another aspect of the invention provides a nucleic acid molecule which hybridizes under selective conditions, e.g. high stringency conditions, to a nucleic acid which comprises a sequence which encodes a GlcNAc-TV-b Protein or GlcNAc-TV-c Protein of the invention. Preferably the sequence encodes an amino acid sequence of SEQ. ID. NO. 2, 4, 6, 10, or 12 and comprises at least 18 nucleotides. Selectivity of hybridization occurs with a certain degree of specificity rather than being random. Appropriate stringency conditions which promote DNA hybridization are known to those skilled in the art, or can be found in Current Protocols in Molecular Biology, John Wiley & Sons, N.Y. (1989), 6.3.1–6.3.6. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g. formamide, dextran sulfate and/or polyethylene glycol), and temperature of the reactions (within a range from about 5° C. below the melting temperature of the probe to about 20° C. to 25° C. below the melting temperature). One or more factors may be varied to generate conditions of either low or high stringency different from, but equivalent to, the above listed conditions. For example, 6.0×sodium chloride/sodium citrate (SSC) or 0.5% SDS at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

It will be appreciated that the invention includes nucleic acid molecules encoding a GlcNAc-TV-b Protein, GlcNAc-TV-b Related Protein, GlcNAc-TV-c Protein, or GlcNAc-TV-c Related Protein, including truncations of the proteins, allelic and species variants, and analogs of the proteins as described herein. In particular, fragments of a nucleic acid molecule of the invention are contemplated that are a stretch of at least about 10, preferably at least 15, more preferably at least 18, and most preferably at least 20 nucleotides, more typically at least 50 to 200 nucleotides but less than 2 kb. It will further be appreciated that variant forms of the nucleic acid molecules of the invention which arise by alternative splicing of an mRNA corresponding to a cDNA of the invention are encompassed by the invention.

An isolated nucleic acid molecule of the invention which comprises DNA can be isolated by preparing a labeled nucleic acid probe based on all or part of a nucleic acid sequence of SEQ. ID. NO. 1, 3, 5, 9, or 11. The labeled nucleic acid probe is used to screen an appropriate DNA library (e.g. a cDNA or genomic DNA library). For example, a cDNA library can be used to isolate a cDNA encoding a GlcNAc-TV-b Protein, a GlcNAc-TV-b Related Protein, a GlcNAc-TV-c Protein, or a GlcNAc-TV-c Related Protein by screening the library with the labeled probe using standard techniques. Alternatively, a genomic DNA library can be similarly screened to isolate a genomic clone encompassing a glcNAc-TV-b or glcNAc-TV-c gene. Nucleic acids isolated by screening of a cDNA or genomic DNA library can be sequenced by standard techniques.

An isolated nucleic acid molecule of the invention which is DNA can also be isolated by selectively amplifying a nucleic acid of the invention. "Amplifying" or "amplification" refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.). In particular, it is possible to design synthetic oligonucleotide primers from a nucleotide sequence of SEQ. ID. NO. 1, 3, 5, 7, 8, 9, or 11 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a GlcNAc-TV-b Protein, GlcNAc-TV-b Related Protein, GlcNAc-TV-c Protein, or GlcNAc-TV-c Related Protein into an appropriate vector which allows for transcription of the cDNA to produce an RNA molecule which encodes a GlcNAc-TV-b Protein, GlcNAc-TV-b Related Protein, GlcNAc-TV-c Protein, or GlcNAc-TV-c Related Protein. For example, a cDNA can be cloned downstream of a bacteriophage promoter, (e.g. a T7 promoter) in a vector, cDNA can be transcribed in vitro with T7 polymerase, and the resultant RNA can be isolated by conventional techniques.

Nucleic acid molecules of the invention may be chemically synthesized using standard techniques. Methods of chemically synthesizing polydeoxynucleotides are known, including but not limited to solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule is a GlcNAc-TV-b or GlcNAc-TV-c or encodes a GlcNAc-TV-b Protein, GlcNAc-TV-b Related Protein, GlcNAc-TV-c Protein, or GlcNAc-TV-c Related Protein can be accomplished by expressing the cDNA in an appropriate host cell by standard techniques, and testing the expressed protein in the methods described herein. A GlcNAc-TV-b or GlcNAc-TV-c cDNA or cDNA encoding a GlcNAc-TV-b Protein, GlcNAc-TV-b Related Protein, GlcNAc-TV-c Protein, or GlcNAc-TV-c Related Protein can be sequenced by standard techniques, such as dideoxynucleotide chain termination or Maxam-Gilbert chemical sequencing, to determine the nucleic acid sequence and the predicted amino acid sequence of the encoded protein.

The initiation codon and untranslated sequences of a nucleic acid molecule of the invention may be determined using computer software designed for the purpose, such as PC/Gene (IntelliGenetics Inc., Calif.). The intron-exon structure and the transcription regulatory sequences of a nucleic acid molecule of the invention and/or encoding a GlcNAc-TV-b Protein, GlcNAc-TV-b Related Protein, GlcNAc-TV-c Protein, or GlcNAc-TV-c Related Protein may be identified by using a nucleic acid molecule of the invention to probe a genomic DNA clone library. Regulatory elements can be identified using standard techniques. The function of the elements can be confirmed by using these elements to express a reporter gene such as the lacZ gene which is operatively linked to the elements. These constructs may be introduced into cultured cells using conventional procedures or into non-human transgenic animal models. In addition to identifying regulatory elements in DNA, such constructs may also be used to identify nuclear proteins interacting with the elements, using techniques known in the art.

In accordance with one aspect of the invention, a nucleic acid is provided comprising a GlcNAc-TV-b regulatory sequence such as a promoter sequence. In particular, an isolated nucleic acid molecule is contemplated which comprises:

(i) a nucleic acid sequence having at least 75% sequence identity with a sequence of SEQ. ID. NO. 7 or 8;

(ii) nucleic acid sequences complementary to (i), (iii) nucleic acid sequences differing from any of the nucleic acids of (i) or (ii) in codon sequences due to the degeneracy of the genetic code;

(iv) a nucleic acid sequence comprising at least 10, most preferably 18 nucleotides and capable of hybridizing under stringent conditions to a nucleic acid sequence of SEQ. ID. NO. 7 or 8, or to a degenerate form thereof;

(v) a fragment, or allelic or species variation of (i), (ii) or (iii).

In a preferred embodiment, the isolated nucleic acid comprises a nucleic acid sequence of SEQ. ID. NO. 7 or 8, wherein T can also be U.

The invention contemplates nucleic acid molecules comprising all or a portion of a nucleic acid of the invention comprising a regulatory sequence of a glcNAc-TV-b gene or a glcNAc-TV-c gene (e.g. SEQ ID Nos: 7 or 8) contained in appropriate vectors. The vectors may contain heterologous nucleic acid sequences. "Heterologous nucleic acid" refers to a nucleic acid not naturally located in the cell, or in a chromosomal site of the cell. Preferably, the heterologous nucleic acid includes a nucleic acid foreign to the cell.

In accordance with another aspect of the invention, the nucleic acids isolated using the methods described herein are mutant glcNAc-TV-b or glcNAc-TV-c gene alleles. For example, the mutant alleles may be isolated from individuals either known or proposed to have a genotype which contributes to the symptoms of cancer. Mutant alleles and mutant allele products may be used in therapeutic and diagnostic methods described herein. For example, a cDNA of a mutant glcNAc-TV-b gene may be isolated using PCR as described herein, and the DNA sequence of the mutant allele may be compared to the normal allele to ascertain the mutation(s) responsible for the loss or alteration of function of the mutant gene product. A genomic library can also be constructed using DNA from an individual suspected of or known to carry a mutant allele, or a cDNA library can be constructed using RNA from tissue known, or suspected to express the mutant allele. A nucleic acid encoding a normal glcNAc-TV-b gene or any suitable fragment thereof, may then be labeled and used as a probe to identify the corresponding mutant allele in such libraries. Clones containing mutant sequences can be purified and subjected to sequence analysis. In addition, an expression library can be constructed using cDNA from RNA isolated from a tissue of an individual known or suspected to express a mutant glcNAc-TV-b allele. Gene products from putatively mutant tissue may be expressed and screened, for example using antibodies specific for a GlcNAc-TV-b Protein or a GlcNAc-TV-b Related Protein as described herein. Library clones identified using the antibodies can be purified and subjected to sequence analysis.

Antisense molecules and ribozymes are contemplated within the scope of the invention. "Antisense refers to any composition containing nucleotide sequences which are complementary to a specific DNA or RNA sequence. Ribozymes are enzymatic RNA molecules that can be used to catalyze the specific cleavage of RNA. Antisense molecules and ribozymes may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding a GlcNAc-TV-b Protein, GlcNAc-TV-b Related Protein, GlcNAc-TV-c Protein, or GlcNAc-TV-c Related Protein. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Proteins of the Invention

The proteins of the invention are predominantly expressed in the central nervous system, with the exception of the spinal cord. The proteins are also expressed in different tumors such as cervical carcinoma, lung carcinoma, colon carcinoma, melanoma, and they have been specifically found in tumors from the breast and uterus.

The amino acid sequence of an isolated GlcNAc-TV-b Protein of the invention comprises a sequence of SEQ. ID. NO. 2, 4, or 6. The amino acid sequence of an isolated GlcNAc-TV-c Protein of the invention comprises a sequence of SEQ. ID. NO. 2, 10, or 12. In addition to proteins comprising an amino acid sequence of SEQ. ID. NO. 2, 4, 6, 10, or 12 the proteins of the present invention include truncations, and analogs, allelic and species variations, and homologs of GlcNAc-TV-b or GlcNAc-TV-c and truncations thereof as described herein (i.e. GlcNAc-TV-b Related Proteins or GlcNAc-TV-c Related Proteins).

Truncated proteins may comprise peptides of between 3 and 70 amino acid residues, ranging in size from a tripeptide to a 70 mer polypeptide, preferably 12 to 20 amino acids. In one aspect of the invention, fragments of a GlcNAc-TV-b or GlcNAc-TV-c protein are provided having an amino acid sequence of at least five consecutive amino acids of SEQ. ID. NO. 2, 4, 6, 10, or 12 where no amino acid sequence of five or more, six or more, seven or more, or eight or more, consecutive amino acids present in the fragment is present in a protein other than GlcNAc-TV-b or GlcNAc-TV-c. In an embodiment of the invention the fragment is a stretch of amino acid residues of at least 12 to 20 contiguous amino acids from particular sequences such as the sequence of SEQ. ID. NO. 2, 4, 6, 10, or 12. The fragments may be immunogenic and preferably are not immunoreactive with antibodies that are immunoreactive to proteins other than GlcNAc-TV-b or GlcNAc-TV-c.

The truncated proteins may have an amino group (-NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end.

The proteins of the invention may also include analogs of GlcNAc-TV-b or GlcNAc-TV-c, and/or truncations thereof as described herein, which may include, but are not limited to GlcNAc-TV-b or GlcNAc-TV-c, containing one or more amino acid substitutions, insertions, and/or deletions. Amino acid substitutions may be of a conserved or non-conserved nature. Conserved amino acid substitutions involve replacing one or more amino acids of the GlcNAc-TV-b or GlcNAc-TV-c amino acid sequence with amino acids of similar charge, size, and/or hydrophobicity characteristics. When only conserved substitutions are made the resulting analog is preferably functionally equivalent to GlcNAc-TV-b or GlcNAc-TV-c. Non-conserved substitutions involve replacing one or more amino acids or the GlcNAc-TV-b or GlcNAc-TV-c amino acid sequence with one or more amino acids which possess dissimilar charge, size, and/or hydrophobicity characteristics.

One or more amino acid insertions may be introduced into a GlcNAc-TV-b Protein or GlcNAc-TV-c Protein. Amino acid insertions may consist of single amino acid residues or sequential amino acids ranging from 2 to 15 amino acids in length.

Deletions may consist of the removal of one or more amino acids, or discrete portions from the GlcNAc-TV-b or GlcNAc-TV-c amino acid sequence. The deleted amino acids may or may not be contiguous. The lower limit length of the resulting analog with a deletion mutation is about 10 amino acids, preferably 100 amino acids.

An allelic variant of GlcNAc-TV-b or GlcNAc-TV-c at the protein level differs from one another by only one, or at most, a few amino acids substitutions. A species variation of a GlcNAc-TV-b Protein or GlcNAc-TV-c Protein is a variation which is naturally occurring among different species of an organism.

The proteins of the invention also include homologs of GlcNAc-TV-b or GlcNAc-TV-c and/or truncations thereof as described herein. Such GlcNAc-TV-b or GlcNAc-TV-c homologs include proteins whose amino acid sequences are comprised of the amino acid sequences of GlcNAc-TV-b or GlcNAc-TV-c regions from other species that hybridize under selective hybridization conditions (see discussion of selective and in particular stringent hybridization conditions herein) with a probe used to obtain a GlcNAc-TV-b Protein or GlcNAc-TV-c Protein. These homologs will generally have the same regions which are characteristic of a GlcNAc-TV-b or GlcNAc-TV-c Protein. It is anticipated that a protein comprising an amino acid sequence which has at least 70% identity, more preferably at least 75% identity, most preferably 80 to 90% identity, with an amino acid sequence of SEQ. ID. NO. 2, 4, 6, 10, or 12 will be a homolog of a protein of the invention. A percent amino acid sequence homology or identity is calculated using the methods described herein, preferably the computer programs described herein.

The invention also contemplates isoforms of the proteins of the invention. An isoform contains the same number and kinds of amino acids as the protein of the invention, but the isoform has a different molecular structure. The isoforms contemplated by the present invention preferably have the same properties as the protein of the invention as described herein.

The present invention also includes GlcNAc-TV-b Proteins, GlcNAc-TV-b Related Proteins, GlcNAc-TV-c Proteins, or GlcNAc-TV-c Related Proteins conjugated with a selected protein, or a marker protein (see below), or other glycosyltransferase, to produce fusion proteins or chimeric proteins.

A GlcNAc-TV-b Protein, a GlcNAc-TV-b Related Protein, a GlcNAc-TV-c Protein, or a GlcNAc-TV-c Related Protein of the invention may be prepared using recombinant DNA methods. Accordingly, the nucleic acids of the present invention having a sequence which encodes a GlcNAc-TV-b Protein, a GlcNAc-TV-b Related Protein, a GlcNAc-TV-c Protein, or a GlcNAc-TV-c Related Protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used.

The invention therefore contemplates a recombinant expression vector of the invention containing a nucleic acid molecule of the invention, and the necessary regulatory sequences for the transcription and translation of the inserted protein-sequence. Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. The necessary regulatory sequences may be supplied by the native GlcNAc-TV Protein and/or its flanking regions.

The invention further provides a recombinant expression vector comprising a nucleic acid molecule of the invention cloned into the expression vector in an antisense orientation. That is, the DNA molecule is linked to a regulatory sequence in a manner which allows for expression, by transcription of the DNA molecule, of an RNA molecule which is antisense to a nucleic acid sequence of SEQ. ID. NO. 1, 3, 5, 7, 8, 9, or 11. Regulatory sequences linked to the antisense nucleic acid can be chosen which direct the continuous expression of the antisense RNA molecule in a variety of cell types, for instance a viral promoter and/or enhancer, or regulatory sequences can be chosen which direct tissue or cell type specific expression of antisense RNA.

The recombinant expression vectors of the invention may also contain a marker gene which facilitates the selection of host cells transformed or transfected with a recombinant molecule of the invention. Examples of marker genes are genes encoding a protein such as G418, dhfr, npt, als, pat and hygromycin which confer resistance to certain drugs, β-galactosidase, chloramphenicol acetyltransferase, firefly luciferase, trpB, hisD, herpes simplex virus thymidine kinase, adenine phosphoribosyl transferase, or an immunoglobulin or portion thereof such as the Fc portion of an immunoglobulin preferably IgG. Visible markers such as anthocyanins, beta-glucuronidase and its substrate GUS, and luciferase and its substrate luciferin, can be used to identify transformants, and also to quantify the amount of transient or stable protein expression attributable to a specific vector system (Rhodes, C. et al. (1995) Mol. Biol. 55:121–131). The markers can be introduced on a separate vector from the nucleic acid of interest.

The recombinant expression vectors may also contain genes that encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

The vectors may be introduced into host cells to produce a transformed or transfected host cell. The terms "transfected" and "transfection" encompass the introduction of nucleic acid (e.g. a vector) into a cell by one of many standard techniques. A cell is "transformed" by a nucleic acid when the transfected nucleic acid effects a phenotypic change. Prokaryotic cells can be transfected or transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Human artificial chromosomes (HACs) may also be employed to deliver larger fragments of DNA that can be contained and expressed in a plasmid. HACs of 6 to 10M are constructed and delivered via conventional delivery methods (liposomes, polycationic amino polymers, or vesicles) for therapeutic purposes.

Suitable host cells include a wide variety of prokaryotic and eukaryotic host cells. For example, the proteins of the invention may be expressed in bacterial cells such as *E. coli*, insect cells (using baculovirus), yeast cells, or mammalian cells. Other suitable host cells can be found in Goeddel, Gene Expression Technology: Methods in Enzymology 185, Academic Press, San Diego, Calif. (1991).

A host cell may also be chosen which modulates the expression of an inserted nucleic acid sequence, or modifies (e.g. glycosylation or phosphorylation) and processes (e.g. cleaves) the protein in a desired fashion. Host systems or cell lines may be selected which have specific and characteristic mechanisms for post-translational processing and modification of proteins. For example, eukaryotic host cells including CHO, VERO, BHK, A431, HeLA, COS, MDCK, 293, 3T3, and W138 may be used. For long-term high-yield stable expression of the protein, cell lines and host systems which stably express the gene product may be engineered.

Host cells and in particular cell lines produced using the methods described herein may be particularly useful in screening and evaluating compounds that modulate the activity of GlcNAc-TV-b Protein, GlcNAc-TV-b Related Protein, GlcNAc-TV-c Protein, or a GlcNAc-TV-c Related Protein.

The proteins of the invention may also be expressed in non-human transgenic animals including but not limited to mice, rats, rabbits, guinea pigs, micro-pigs, goats, sheep, pigs, non-human primates (e.g. baboons, monkeys, and chimpanzees) (see Hammer et al. (Nature 315: 680–683, 1985), Palmiter et al. (Science 222:809–814, 1983), Brinster et al. (Proc Natl. Acad. Sci USA 82:44384442, 1985), Palmiter and Brinster (Cell. 41:343–345, 1985) and U.S. Pat. No. 4,736,866). Procedures known in the art may be used to introduce a nucleic acid molecule of the invention encoding a GlcNAc-TV-b Protein, GlcNAc-TV-b Related Protein, a GlcNAc-TV-c Protein, or a GlcNAc-TV-c Related Protein into animals to produce the founder lines of transgenic animals. Such procedures include pronuclear microinjection, retrovirus mediated gene transfer into germ lines, gene targeting in embryonic stem cells, electroporation of embryos, and sperm-mediated gene transfer.

The present invention contemplates a transgenic animal that carries the GlcNAc-TV-b or GlcNAc-TV-c gene in all their cells, and animals which carry the transgene in some but not all their cells. The transgene may be integrated as a single transgene or in concatamers. The transgene may be selectively introduced into and activated in specific cell types (See for example, Lasko et al, 1992 Proc. Natl. Acad. Sci. USA 89: 6236). The transgene may be integrated into the chromosomal site of the endogenous gene by gene targeting. The transgene may be selectively introduced into a particular cell type inactivating the endogenous gene in that cell type (See Gu et al Science 265: 103–106).

The expression of a recombinant GlcNAc-TV-b Protein, GlcNAc-TV-b Related Protein, GlcNAc-TV-c Protein, or GlcNAc-TV-c Related Protein in a transgenic animal may be assayed using standard techniques. Initial screening may be conducted by Southern Blot analysis, or PCR methods to analyze whether the transgene has been integrated. The level of mRNA expression in the tissues of transgenic animals may also be assessed using techniques including Northern blot analysis of tissue samples, in situ hybridization, and RT-PCR. Tissue may also be evaluated immunocytochemically using antibodies against a GlcNAc-TV-b Protein or GlcNAc-TV-c Protein of the invention.

Proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. I5 1 and II, Thieme, Stuttgart). Protein synthesis may be performed using manual procedures or by automation. Automated synthesis may be carried out, for example, using an Applied Biosystems 431A peptide synthesizer (Perkin Elmer). Various fragments of the proteins of the invention may be chemically synthesized separately and combined using chemical methods to produce the full length molecule.

N-terminal or C-terminal fusion proteins or chimeric proteins comprising a GlcNAc-TV-b Protein, GlcNAc-TV-b Related Protein, a GlcNAc-TV-c Protein, or a GlcNAc-TV-c Related Protein of the invention conjugated with other molecules, such as proteins (e.g. markers or other glycosyltransferases) may be prepared by fusing, through recombinant techniques, the N-terminal or C-terminal of a GlcNAc-TV-b Protein, a GlcNAc-TV-b Related Protein, a GlcNAc-TV-c Protein, or a GlcNAc-TV-c Related Protein, and the sequence of a selected protein or marker protein with a desired biological function. The resultant fusion proteins contain a GlcNAc-TV-b Protein, a GlcNAc-TV-b Related Protein, a GlcNAc-TV-c Protein, or a GlcNAc-TV-c Related Protein fused to the selected protein or marker protein as described herein. Examples of proteins which may be used to prepare fusion proteins include immunoglobulins, glutathione-S-transferase (GST), protein A, hemagglutinin (HA), and truncated myc.

Antibodies

A protein of the invention, or a portion thereof can be used to prepare antibodies specific for the proteins. Antibodies can be prepared which bind a distinct epitope in an unconserved region of the protein. An unconserved region of the protein is one that does not have substantial sequence homology to other proteins. A region from a conserved region such as a well-characterized domain can also be used to prepare an antibody to a conserved region of a protein of the invention.

In an embodiment of the invention, oligopeptides, peptides, or fragments used to induce antibodies to a protein of the invention have an amino acid sequence consisting of at least 5 amino acids and more preferably at least 10 amino acids. The oligopeptides, etc. can be identical to a portion of the amino acid sequence of the natural protein, and they may contain the entire amino acid sequence of a small, naturally occurring molecule. Antibodies having specificity for a protein of the invention may also be raised from fusion proteins created by expressing fusion proteins in bacteria as described herein.

The invention can employ intact monoclonal or polyclonal antibodies, and immunologically active fragments (e.g. a Fab or (Fab)$_2$ fragment), an antibody heavy chain, an antibody light chain, a genetically engineered single chain F$_V$ molecule (Ladner et al, U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, etc. may be prepared using methods known to those skilled in the art.

Applications of the Nucleic Acid Molecules, Proteins, and Antibodies of the Invention The nucleic acid molecules, GlcNAc-TV-b Proteins, GlcNAc-TV-b Related Proteins, GlcNAc-TV-c Proteins, or GlcNAc-TV-c Related Proteins, and antibodies of the invention may be used in the prognostic and diagnostic evaluation of conditions requiring modulation of a nucleic acid or protein of the invention including cancer, and the identification of subjects with a predisposition to such conditions (See below). Methods for detecting nucleic acid molecules and proteins of the invention, can be used to monitor conditions requiring modulation of the nucleic acids or proteins including cancer (e.g. solid tumors, such as breast and uterine cancer) by detecting and localizing the proteins and nucleic acids. It would also be apparent to one skilled in the art that the methods described herein may be used to study the developmental expression of the proteins of the invention and, accordingly, will provide further insight into the role of the proteins. The applications of the present invention also include methods for the identification of compounds which modulate the biological activity of a protein of the invention (See below). The compounds, antibodies, etc. may be used for the treatment of conditions requiring modulation of proteins of the invention including cancer (e.g. solid tumors, such as breast and uterine cancer). (See below).

Diagnostic Methods

A variety of methods can be employed for the diagnostic and prognostic evaluation of conditions requiring modulation of a nucleic acid or protein of the invention including cancer (e.g. solid tumors, breast and uterine cancer), and the identification of subjects with a predisposition to such conditions. Such methods may, for example, utilize nucleic acid molecules of the invention, and fragments thereof, and antibodies directed against proteins of the invention, including peptide fragments. In particular, the nucleic acids and antibodies may be used, for example, for: (1) the detection of the presence of glcNAc-TV-b or glcNAc-TV-c mutations, or the detection of either over- or under-expression of GlcNAc-TV-b or GlcNAc-TV-c mRNA relative to a non-disorder state or the qualitative or quantitative detection of alternatively spliced forms of glcNAc-TV-b or glcNAc-TV-c transcripts which may correlate with certain conditions or susceptibility toward such conditions; and (2) the detection of either an over- or an under-abundance of a protein of the invention relative to a non-disorder state or the presence of a modified (e.g., less than full length) protein of the invention which correlates with a disorder state, or a progression toward a disorder state.

The methods described herein may be performed by utilizing pre-packaged diagnostic kits comprising at least one specific nucleic acid or antibody described herein, which may be conveniently used, e.g., in clinical settings, to screen and diagnose patients and to screen and identify those individuals exhibiting a predisposition to developing a disorder.

Nucleic acid-based detection techniques and peptide detection techniques are described below. The samples that may be analyzed using the methods of the invention include those which are known or suspected to express glcNAc-TV-b or glcNAc-TV-c or contain a protein of the invention. The methods may be performed on biological samples including but not limited to cells, lysates of cells which have been incubated in cell culture, chromosomes isolated from a cell (e.g. a spread of metaphase chromosomes), genomic DNA (in solutions or bound to a solid support such as for Southern analysis), RNA (in solution or bound to a solid support such as for northern analysis), cDNA (in solution or bound to a solid support), an extract from cells or a tissue, and biological fluids such as serum, urine, blood, and CSF. The samples may be derived from a patient or a culture.

Methods for Detecting Nucleic Acid Molecules of the Invention

A nucleic acid molecule encoding a protein of the invention may be used in Southern or northern analysis, dot blot, or other membrane-based technologies; in PCR technologies; or in dipstick, pin, ELISA assays or microarrays utilizing fluids or tissues from patient biopsies to detect altered expression. Such qualitative or quantitative methods are well known in the art and some methods are described below.

The nucleic acid molecules of the invention allow those skilled in the art to construct nucleotide probes for use in the detection of nucleic acid sequences of the invention in biological materials. Suitable probes include nucleic acid molecules based on nucleic acid sequences encoding at least 5 sequential amino acids from regions of the GlcNAc-TV-b or GlcNAc-TV-c nucleic acid molecules (see SEQ. ID. No. 1, 3, 5, 7, 8, 9, or 11), preferably they comprise 15 to 30 nucleotides. A nucleotide probe may be labeled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect glcNAc-TV-b or GlnNAc-TV-c genes, preferably in human cells. The nucleotide probes may also be useful for example in the diagnosis or prognosis of cancer, the staging of the cancer, and in monitoring the progression of these conditions, or monitoring a therapeutic treatment. The probes may also be useful for mapping the naturally occurring genomic sequence. Sequences can be mapped to a particular chromosome, to a specific region of a chromosome, or to an artificial chromosome construction (e.g. HACs, yest artificial chromosomes (YACs), bacterial artificial chromosomes (BACs) bacterial P1 constructions or single chromosome cDNA libraries (see Price, C. M. 1993, Blood Rev. 7:127–1134 and Trask, B. J. 1991, Trends Genet. 7;149–154).

The probe may be used in hybridization techniques to detect glcNAc-TV-b or glcNAc-TV-c genes. The technique generally involves contacting and incubating nucleic acids (e.g. recombinant DNA molecules, cloned genes) obtained from a sample from a patient or other cellular source with a probe of the present invention under conditions favourable for the specific annealing of the probes to complementary sequences in the nucleic acids. After incubation, the non-annealed nucleic acids are removed, and the presence of nucleic acids that have hybridized to the probe if any are detected.

The detection of nucleic acid molecules of the invention may involve the amplification of specific gene sequences using an amplification method such as PCR, followed by the analysis of the amplified molecules using techniques known to those skilled in the art. Suitable primers can be routinely designed by one of skill in the art.

Genomic DNA may be used in hybridization or amplification assays of biological samples to detect abnormalities involving glcNAc-TV-b or glcNAc-TV-c structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a glcNAc-TV-b or glcNAc-TV-c gene. The polymorphisms may be used to identify individuals in families that are likely to carry mutations. If a polymorphism exhibits linkage disequalibrium with mutations in the glcNAc-TV-b or glcNAc-TV-c genes, it can also be used to screen for individuals in the general population likely to carry mutations. Polymorphisms which may be used include restriction fragment length polymorphisms (RFLPs), single-base polymorphisms, and simple sequence repeat polymorphisms (SSLPs).

A probe of the invention may be used to directly identify RFLPs. A probe or primer of the invention can additionally be used to isolate genomic clones such as YACs, BACs, PACs, cosmids, phage or plasmids. The DNA in the clones can be screened for SSLPs using hybridization or sequencing procedures.

Hybridization and amplification techniques described herein may be used to assay qualitative and quantitative aspects of glcNAc-TV-b or glcNAc-TV-c expression. For example, RNA may be isolated from a cell type or tissue known to express glcNAc-TV-b (e.g. brain) and tested utilizing the hybridization (e.g. standard Northern analyses) or PCR techniques referred to herein. The techniques may be used to detect differences in transcript size which may be due to normal or abnormal alternative splicing. The techniques may be used to detect quantitative differences between levels of full length and/or alternatively splice transcripts detected in normal individuals relative to those individuals exhibiting symptoms of a disease such as cancer.

The primers and probes may be used in the above described methods in situ i.e. directly on tissue sections (fixed and/or frozen) of patient tissue obtained from biopsies or resections.

Microarrays

Oligonucleotides derived from any of the nucleic acid molecules of the invention may be used as targets in microarrays. "Microarray" refers to an array of distinct polynucleotides or oligonucleotides synthesized on a substrate, such as paper, nylon, or other type of membrane, filter, chip, glass slide, or any other suitable solid support.

The microarrays can be used to monitor the expression level of large numbers of genes simultaneously (to produce a transcript image) and to identify genetic variants, mutations, and polymorphisms. This information can be useful in determining gene function, understanding the genetic basis of disease, diagnosing disease, and in developing and monitoring the activity of therapeutic agents (Heller, R. et al. (1997) Proc. Natl. Acad, Sci. 94:2150–55).

In an embodiment of the invention, the microarray is prepared and used according to the methods described in PCT application WO95/11995 (Chee et al), Lockhart D. J. et al, 1996, Nat. Biotech. 14:1675–1680) and Schena M. et al 1996, Proc. Natl. Acad, Sic. 93: 10614–10619).

The microarray can be composed of a large number of unique, single-stranded nucleic acid sequences, usually either synthetic antisense oligonucleotides or fragments of cDNAs fixed to a solid support. The oligonucleotides can be about 6–60 nucleotides in length, preferably 15–30 nucleotides in length, and most preferably about 20–25 nucleotides in length. For some microarrays it may be preferred to use oligonucleotides which are about 7–10 nucleotides in length. The microarray can contain oligonucleotides covering the known 5' or 3' sequence, sequential oligonucleotides covering the full length sequence, or unique oligonucleotides selected from particular areas along the length of the sequence. Polynucleotides used in the microarray can be oligonucleotides specific to a gene(s) of interest in which at least a fragment of the sequence is known or that are specific to one or more unidentified cDNAs which are common to particular cell types, or developmental or disease state.

To produce oligonucleotides to a known sequence for a microarray, a gene of interest is examined using a computer algorithm which starts at the 5' or more preferably at the 3' end of the nucleotide sequence. The algorithm identifies oligomers of a defined length that are unique to the gene, have a GC content within a suitable range for hybridization, and lack predicted secondary structure that can interfere with hybridization. In some cases it may be appropriate to use pairs of oligonucleotides on a microarray. The "pairs" will be identical, except for a single nucleotide which can be located in the center of the sequence. The second oligonucleotide in the pair serves as a control. The number of oligonucleotide pairs may range from two to one million. The oligomers are synthesized at designated areas on a substrate using a light-directed chemical process.

The oligomers can be synthesized on the surface of the substrate by using a chemical coupling procedure and an ink jet application apparatus, such as described in PCT application WO95/251116 (Baldeschweiler et al.). A "gridded" array analogous to a dot (or slot) blot can also be used to arrange and link cDNA fragments or oligonucleotides to the surface of a substrate using a vacuum system, thermal. UV, mechanical or chemical bonding procedures. An array can be produced by hand or using available devices (slot blot or dot blot apparatus), materials (any suitable solid support), and machines (including robotic instruments) and it can contain 8, 24, 96, 384, 1536 or 6144 oligonucleotides, or any other multiple between two and one million which lends itself to the efficient use of commercially available instrumentation.

Sample analysis using microarrays, is conducted by making RNA or DNA from a biological sample into hybridization probes. The mRNA is isolated, and cDNA is prepared and used as a template to make antisense RNA (aRNA). The aRNA is amplified in the presence of fluorescent nucleotides, and labeled hybridization probes are incubated with the microarray so that the probe sequences hybridize to complementary oligonucleotides of the microarray. Incubation conditions are selected so that hybridization occurs with precise complementary matches or with various degrees of less complementarity. After removal of nonhybridized probes, a scanner determines the levels and patterns of fluorescence. The scanned images are examined to determine the degree of complementarity and the relative quantity of each oligonucleotide sequence of the microarray. The biological samples may be obtained from any bodily fluids (such as blood, urine, saliva, phlegm, gastric juices, etc.), cultured cells, biopsies, or other tissue preparations. A detection system can be used to measure the absence, presence, and amount of hybridization for all of the distinct sequences simultaneously. This data can be used for large scale correlation studies on the sequences, mutations, variants, or polymorphisms among samples.

Methods for Detecting Proteins

Antibodies specifically reactive with a GlcNAc-TV-b Protein, a GlcNAc-TV-b Related Protein, a GlcNAc-TV-c Protein, or a GlcNAc-TV-c Related Protein, or derivatives, such as enzyme conjugates or labeled derivatives, may be used to detect GlcNAc-TV-b Proteins, GlcNAc-TV-b Related Proteins, GlcNAc-TV-c Proteins, or GlcNAc-TV-c Related Proteins in various biological materials. They may be used as diagnostic or prognostic reagents and they may be used to detect abnormalities in the level of GlcNAc-TV-b Proteins, GlcNAc-TV-b Related Proteins, GlcNAc-TV-c Proteins, or GlcNAc-TV-c Related Proteins, expression, or abnormalities in the structure, and/or temporal, tissue, cellular, or subcellular location of the proteins. Antibodies may also be used to screen potentially therapeutic compounds in vitro to determine their effects on a condition such as cancer etc. In vitro immunoassays may also be used to assess or monitor the efficacy of particular therapies. The antibodies of the invention may also be used in vitro to determine the level of GlcNAc-TV-b or GlcNAc-TV-c expression in cells genetically engineered to produce a GlcNAc-TV-b Protein, a GlcNAc-TV-b Related Protein, a GlcNAc-TV-c Protein, or a GlcNAc-TV-b Related Protein.

The antibodies may be used in any known immunoassays which rely on the binding interaction between an antigenic determinant of a protein of the invention, and the antibodies. Examples of such assays are radioimmunoassays, enzyme immunoassays (e.g. ELISA), immunofluorescence, immunoprecipitation, latex agglutination, hemagglutination, and histochemical tests. The antibodies may be used to detect and quantify proteins of the invention in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect a protein of the invention, to localise it to particular cells and tissues, and to specific subcellular locations, and to quantitate the level of expression.

Cytochemical techniques known in the art for localizing antigens using light and electron microscopy may be used to detect a protein of the invention. Generally, an antibody of the invention may be labeled with a detectable substance and a protein may be localised in tissues and cells based upon the presence of the detectable substance. Various methods of labeling polypeptides and glycoproteins are known in the art and may be used. Examples of detectable substances include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, β-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against a protein of the invention. By way of example, if the antibody having specificity against a protein of the invention is a rabbit IgG antibody, the second antibody may be goat anti-rabbit gamma-globulin labelled with a detectable substance as described herein.

Where a radioactive label is used as a detectable substance, a protein of the invention may be localized by radioautography. The results of radioautography may be quantitated by determining the density of particles in the radioautographs by various optical methods, or by counting the grains.

Methods for Identifying or Evaluating Substances/Compounds

The methods described herein are designed to identify substances that modulate the biological activity of a GlcNAc-TV-b Protein, GlcNAc-TV-b Related Protein, GlcNAc-TV-c Protein, or GlcNAc-TV-c Related Protein including substances that interfere with, or enhance the activity of a GlcNAc-TV-b Protein, GlcNAc-TV-b Related Protein, GlcNAc-TV-c Protein, or GlcNAc-TV-c Related Protein.

The substances and compounds identified using the methods of the invention include but are not limited to peptides such as soluble peptides including Ig-tailed fusion peptides, members of random peptide libraries and combinatorial chemistry-derived molecular libraries including libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], and small organic or inorganic molecules. The substance or compound may be an endogenous physiological compound or it may be a natural or synthetic compound.

Substances which modulate a GlcNAc-TV-b Protein, GlcNAc-TV-b Related Protein, GlcNAc-TV-c Protein, or GlcNAc-TV-c Related Protein can be identified based on their ability to associate with (or bind to) a GlcNAc-TV-b Protein, GlcNAc-TV-b Related Protein, GlcNAc-TV-c Protein, or GlcNAc-TV-c Related Protein. Therefore, the invention also provides methods for identifying substances which associate with a GlcNAc-TV-b Protein, GlcNAc-TV-b Related Protein, GlcNAc-TV-c Protein, or GlcNAc-TV-c Related Protein. Substances identified using the methods of the invention may be isolated, cloned and sequenced using conventional techniques. A substance that associates with a protein of the invention may be an agonist or antagonist of the biological or immunological activity of a polypeptide of the invention.

The term "agonist", refers to a molecule that increases the amount of, or prolongs the duration of, the activity of the protein. The term "antagonist" refers to a molecule which decreases the biological or immunological activity of the protein. Agonists and antagonists may include proteins, nucleic acids, carbohydrates, or any other molecules that associate with a polypeptide of the invention.

Substances which can associate with a GlcNAc-TV-b Protein, GlcNAc-TV-b Related Protein, GlcNAc-TV-c Protein, or GlcNAc-TV-c Related Protein may be identified by reacting a GlcNAc-TV-b Protein, GlcNAc-TV-b Related Protein, GlcNAc-TV-c Protein, or GlcNAc-TV-c Related Protein with a test substance which potentially associates with a GlcNAc-TV-b Protein, GlcNAc-TV-b Related Protein, GlcNAc-TV-c Protein, or GlcNAc-TV-c Related Protein, under conditions which permit the association, and removing and/or detecting GlcNAc-TV-b Protein, GlcNAc-TV-b Related Protein, GlcNAc-TV-c Protein, or GlcNAc-TV-c Related Protein associated with the test substance. Substance-protein complexes, free substance, or non-complexed protein may be assayed. Conditions which permit the formation of substance-protein complexes may be selected having regard to factors such as the nature and amounts of the substance and the protein.

The substance-protein complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against a protein of the invention or the substance, or labeled protein, or a labeled substance may be utilized. The antibodies, proteins, or substances may be labeled with a detectable substance as described above.

A GlcNAc-TV-b Protein, GlcNAc-TV-b Related Protein, GlcNAc-TV-c Protein, or GlcNAc-TV-c Related Protein, or the substance used in the method of the invention may be insolubilized. For example, a protein, or substance may be bound to a suitable carrier such as agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc. The insolubilized protein or substance may be prepared by reacting the material with a suitable insoluble carrier using known chemical or physical methods, for example, cyanogen bromide coupling.

The invention also contemplates a method for evaluating a compound for its ability to modulate the biological activity of a protein of the invention, by assaying for an agonist or antagonist (i.e. enhancer or inhibitor) of the association of the protein with a substance which associates with the protein. The basic method for evaluating if a compound is an agonist or antagonist of the association of a protein of the invention and a substance that associates with the protein, is to prepare a reaction mixture containing the protein and the substance under conditions which permit the formation of substance-protein complexes, in the presence of a test compound. The test compound may be initially added to the mixture, or may be added subsequent to the addition of the protein and substance. Control reaction mixtures without the test compound or with a placebo are also prepared. The formation of complexes is detected and the formation of complexes in the control reaction but not in the reaction mixture indicates that the test compound interferes with the interaction of the protein and substance. The reactions may be carried out in the liquid phase or the protein, substance, or test compound may be immobilized as described herein.

It will be understood that the agonists and antagonists i.e. inhibitors and enhancers that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of the interaction of a protein of the invention with a substance which is capable of binding to the protein. Thus, the invention may be used to assay for a compound that competes for the same binding site of a protein of the invention.

Substances that modulate a GlcNAc-TV-b Protein, GlcNAc-TV-b Related Protein, GlcNAc-TV-c Protein, or GlcNAc-TV-c Related Protein of the invention can be identified based on their ability to interfere with or enhance the activity of a GlcNAc-TV-b Protein, GlcNAc-TV-b Related Protein, GlcNAc-TV-c Protein, or GlcNAc-TV-c Related Protein. Therefore, the invention provides a method for evaluating a compound for its ability to modulate the activity of a GlcNAc-TV-b Protein, GlcNAc-TV-b Related Protein, GlcNAc-TV-c Protein, or GlcNAc-TV-c Related Protein comprising (a) reacting an acceptor and a sugar donor for a GlcNAc-TV-b Protein, GlcNAc-TV-b Related Protein, GlcNAc-TV-c Protein, or GlcNAc-TV-c Related Protein in the presence of a test substance; (b) measuring the amount of sugar donor transferred to acceptor, and (c) carrying out steps (a) and (b) in the absence of the test substance to determine if the substance interferes with or enhances transfer of the sugar donor to the acceptor by the GlcNAc-TV-b Protein, GlcNAc-TV-b Related Protein, GlcNAc-TV-c Protein, or GlcNAc-TV-c Related Protein.

Suitable acceptors for use in the method of the invention are a saccharide, oligosaccharides, polysaccharides, glycopeptides, glycoproteins, or glycolipids which are either synthetic with linkers at the reducing end or naturally occurring structures, for example, asialo-agalacto-fetuin glycopeptide.

The sugar donor may be a nucleotide sugar, dolichol-phosphate-sugar or dolichol-pyrophosphate-oligosaccharide, for example, uridine diphospho-N-acetylglucosamine (UDP-GlcNAc), or derivatives or analogs thereof. The GlcNAc-TV-b Protein, GlcNAc-TV-b Related Protein, GlcNAc-TV-c Protein, or GlcNAc-TV-c Related Protein may be obtained from natural sources or produced used recombinant methods as described herein.

The acceptor or sugar donor may be labeled with a detectable substance as described herein, and the interaction of the protein of the invention with the acceptor and sugar donor will give rise to a detectable change. The detectable change may be colorimetric, photometric, radiometric, potentiometric, etc. The activity of a GlcNAc-TV-b Protein, GlcNAc-TV-b Related Protein, GlcNAc-TV-c Protein, or GlcNAc-TV-c Related Protein of the invention may also be determined using methods based on HPLC (Koenderman et al., FEBS Lett. 222:42, 1987) or methods employed synthetic oligosaccharide acceptors attached to hydrophobic aglycones (Palcic et al Glycoconjugate 5:49, 1988; and Pierce et al. Biochem. Biophys. Res. Comm. 146:679, 1987).

The GlcNAc-TV-b Protein, GlcNAc-TV-b Related Protein, GlcNAc-TV-c Protein, or GlcNAc-TV-c Related Protein is reacted with the acceptor and sugar donor at a pH and temperature and in the presence of a metal cofactor, usually a divalent cation like manganese, effective for the protein to transfer the sugar donor to the acceptor, and where one of the components is labeled, to produce a detectable change. It is preferred to use a buffer with the acceptor and sugar donor to maintain the pH within the pH range effective for the proteins. The buffer, acceptor and sugar donor may be used as an assay composition. Other compounds such as EDTA and detergents may be added to the assay composition.

The reagents suitable for applying the methods of the invention to evaluate compounds that modulate a GlcNAc-TV-b Protein, GlcNAc-TV-b Related Protein, GlcNAc-TV-c Protein, or GlcNAc-TV-c Related Protein may be packaged into convenient kits providing the necessary materials packaged into suitable containers. The kits may also include suitable supports useful in performing the methods of the invention.

Compositions and Treatments

The nucleic acid molecules and proteins of the invention and substances or compounds identified by the methods described herein, antibodies, and antisense nucleic acid molecules of the invention may be used for modulating the biological activity of a GlcNAc-TV-b Protein, GlcNAc-TV-b Related Protein, GlcNAc-TV-c Protein, or GlcNAc-TV-c Related Protein, and they may be used to treat or prevent cancer, inhibit or treat tumor metastasis, stimulate hematopoietic progenitor cell growth, confer protection against chemotherapy and radiation therapy in a subject, and/or treat proliferative disorders, microbial or parasitic infections, or neurological disorders.

The substances, compounds, etc. of the invention may be especially useful in the treatment of various forms of neoplasia such as melanomas, adenomas, sarcomas, and particularly carcinomas of solid tissues in patients. In particular the composition may be used for treating cervico-uterine cancer, cancer of the kidney, brain, stomach, lung, rectum, breast, bowel, gastric, liver, thyroid, neck, cervix, salivary gland, bile duct, pelvis, mediastinum, urethra, bronchogenic, bladder, esophagus and colon, and Kaposi's Sarcoma which is a form of cancer associated with HIV-infected patients with Acquired Immune Deficiency Syndrome (AIDS).

Accordingly, the proteins, substances, antibodies, and compounds etc. may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactive the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

After pharmaceutical compositions have been prepared, they can be placed in an appropriate container and labeled for treatment of an indicated condition. For administration of a composition of the invention the labeling would include amount, frequency, and method of administration.

The compositions, substances, compounds etc. may be indicated as therapeutic agents either alone or in conjunction with other therapeutic agents or other forms of treatment (e.g. chemotherapy or radiotherapy). They can be used to enhance activation of macrophages, T cells, and NK cells in the treatment of cancer and immunosuppressive diseases. By way of example, they can be used in combination with anti-proliferative agents, antimicrobial agents, immunostimulatory agents, or anti-inflammatories. In particular, they can be used in combination with anti-viral and/or anti-proliferative agents, such as Th1 cytokines including interleukin-2, interleukin-12, and interferon-, and nucleoside analogues such as AZT and 3TC. They can be administered concurrently, separately, or sequentially with other therapeutic agents or therapies.

The nucleic acid molecules encoding a GlcNAc-TV-b Protein, GlcNAc-TV-b Related Protein, GlcNAc-TV-c Protein, or GlcNAc-TV-c Related Protein or any fragment thereof, or antisense sequences may be used for therapeutic purposes. Antisense to a nucleic acid molecule encoding a protein of the invention may be used in situations to block the synthesis of the protein. In particular, cells may be transformed with sequences complementary to nucleic acid molecules encoding a GlcNAc-TV-b Protein, GlcNAc-TV-b Related Protein, GlcNAc-TV-c Protein, or GlcNAc-TV-c Related Protein. Thus, antisense sequences may be used to modulate GlcNAc-TV-b Protein, GlcNAc-TV-b Related Protein, GlcNAc-TV-c Protein, or GlcNAc-TV-c Related Protein activity, or to achieve regulation of gene function. Sense or antisense oligomers or larger fragments, can be designed from various locations along the coding or regulatory regions of sequences encoding a protein of the invention.

Expression vectors may be derived from retroviruses, adenoviruses, herpes or vaccinia viruses or from various bacterial plasmids for delivery of nucleic acid sequences to the target organ, tissue, or cells. Vectors that express antisense nucleic acid sequences of glcNAc-TV-b or glcNAc-TV-c can be constructed using techniques well known to those skilled in the art (see for example, Sambrook et al. (supra)).

Genes encoding a GlcNAc-TV-b Protein, GlcNAc-TV-b Related Protein, GlcNAc-TV-c Protein, or GlcNAc-TV-c Related Protein can be turned off by transforming a cell or tissue with expression vectors that express high levels of a nucleic acid molecule or fragment thereof which encodes a protein of the invention. Such constructs may be used to introduce untranslatable sense or antisense sequences into a cell. Even if they do no integrate into the DNA, the vectors may continue to transcribe RNA molecules until all copies are disabled by endogenous nucleases. Transient expression may last for extended periods of time (e.g a month or more) with a non-replicating vector or if appropriate replication elements are part of the vector system.

Modification of gene expression may be achieved by designing antisense molecules, DNA, RNA, or Peptide nucleic acid (PNA), to the control regions of a glcNAc-TV-b or glcNAc-TV-c gene i.e. the promoters, enhancers, and introns. Preferably the antisense molecules are oligonucleotides derived from the transcription initiation site (e.g. between positions −10 and +10 from the start site). Inhibition can also be achieved by using triple-helix base-pairing techniques. Triple helix pairing causes inhibition of the ability of the double helix to open sufficiently for the binding of polymerases, transcription factors, or regulatory molecules (see Gee J. E. et al (1994) In: Huber, B. E. and B. I. Carr, Molecular and Immunologic Approaches, Futura Publishing Co., Mt. Kisco, N.Y.). An antisense molecule may also be designed to block translation of mRNA by inhibiting binding of the transcript to the ribosomes.

Ribozymes may be used to catalyze the specific cleavage of RNA. Ribozyme action involves sequence-specific hybridization of the ribozyme molecule to complementary target RNA, followed by endonucleolytic cleavage. For example, hammerhead motif ribozyme molecules may be engineered that can specifically and efficiently catalyze endonucleolytic cleavage of sequences encoding a polypeptide of the invention.

Specific ribosome cleavage sites within any RNA target may be initially identified by scanning the target molecule for ribozyme cleavage sites which include the following sequences: GUA, GUU, and GUC. Short RNA sequences of between 15 and 20 ribonucleotides corresponding to the region of the cleavage site of the target gene may be evaluated for secondary structural features which may render the oligonucleotide inoperable. The suitability of candidate targets may be evaluated by testing accessibility to hybridization with complementary oligonucleotides using ribonuclease protection assays.

The activity of the proteins, nucleic acid molecules, substances, compounds, antibodies, antisense nucleic acid molecules, and compositions of the invention may be confirmed in animal experimental model systems.

The invention also provides methods for studying the function of a GlcNAc-TV-b Protein, GlcNAc-TV-b Related Protein, GlcNAc-TV-c Protein, or GlcNAc-TV-c Related Protein. Cells, tissues, and non-human animals lacking in glcNAc-TV-b or glcNAc-TV-c expression or partially lacking in glcNAc-TV-b or glcNAc-TV-c expression may be developed using recombinant expression vectors of the invention having specific deletion or insertion mutations in the glcNAc-TV-b or glcNAc-TV-c gene. A recombinant expression vector may be used to inactivate or alter the endogenous gene by homologous recombination, and thereby create a glcNAc-TV-b or glcNAc-TV-c deficient cell, tissue or animal.

Null alleles may be generated in cells, such as embryonic stem cells by deletion mutation. A recombinant glcNAc-TV-b or glcNAc-TV-c gene may also be engineered to contain an insertion mutation which inactivates glcNAc-TV-b or glcNAc-TV-c. Such a construct may then be introduced into a cell, such as an embryonic stem cell, by a technique such as transfection, electroporation, injection etc. Cells lacking an intact glcNAc-TV-b or glcNAc-TV-c gene may then be identified, for example by Southern blotting, Northern Blotting or by assaying for expression of a protein of the invention using the methods described herein. Such cells may then be used to generate transgenic non-human animals deficient in glcNAc-TV-b or glcNAc-TV-c. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on glcNAc-TV-b or glcNAc-TV-c expression.

A protein of the invention may be used to support the survival, growth, migration, and/or differentiation of cells expressing the polypeptide. Thus, a polypeptide of the invention may be used as a supplement to support, for example cells in culture.

Methods for Preparing Oligosaccharides

The invention relates to a method for preparing an oligosaccharide comprising contacting a reaction mixture comprising an activated GlcNAc and an acceptor in the presence of a protein of the invention.

Examples of acceptors for use in the method for preparing an oligosaccharide are a saccharide, oligosaccharides, polysaccharides, glycopeptides, glycoproteins, or glycolipids which are either synthetic with linkers at the reducing end or naturally occurring structures, for example, asialo-agalacto-fetuin glycopeptide. The activated GlcNAc may be part of a nucleotide-sugar, a dolichol-phosphate-sugar, or dolichol-pyrophosphate-oligosaccharide.

In an embodiment of the invention, the oligosaccharides are prepared on a carrier that is non-toxic to a mammal, in particular a lipid isoprenoid or polyisoprenoid alcohol. An example of a suitable carrier is dolichol phosphate. The oligosaccharide may be attached to a carrier via a labile bond allowing for chemical removal of the oligosaccharide from the lipid carrier. In the alternative, the oligosaccharide transferase may be used to transfer the oligosaccharide form a lipid carrier to a protein.

The following non-limiting examples are illustrative of the present invention.

EXAMPLE 1
Isolation of Human GlcNAc-TVb

A cDNA sequence of a human GlcNAc-TV homolog was identified by similarity matching using the GeneBank EST-database (accession number R87580). This EST cDNA clone (designated as hGTNVb) was sequenced (627 base pairs) and when translated was shown to be 67% identical to the 3' end of the human GlcNAc-TV amino acid sequence. This information initiated a search for the entire sequence of this human GlcNAc-TV-like cDNA using two different methods; screening a human brain cDNA library by colony plaque lifts and 5' RACE (rapid amplification of cDNA ends).

A human brain 5'STRETCH PLUS cDNA library (gt10-CLONTECH (Cat # HL3002A) was screened (using standard protocols) with a $^{32}$P-dCTP labeled 203 base pair cDNA probe generated by restriction enzyme digestions of the hGlcNAc-TV-b EST cDNA with Not1 and BamH1. Two million phage clones were screened and 4 positive clones were identified. Each of these clones was purified to homogeneity by three subsequent rounds of screening and phage DNA was isolated from each of these clones using conventional methods. The cDNA insert was isolated from each of these clones and then subcloned into the EcoR1 site of the Bluescript vector (Stratagene) and sequenced. Two out of four clones had sequences that were identical to the EST clone and thereby provided no new information. The other two clones were found to be similar to hGlcNAc-TV-b. One clone (1820 base pairs) was identical in sequence to the coding region of the EST clone with an additional 1295 base pairs of 3' untranslated sequence and the other clone was 61% identical (amino acid comparison) with hGlcNAc-TV-b and was designated as hGlcNAc-TV-c. Interestingly the 3' ends of hGlcNAc-TV-b and hGlcNAc-TV-c are very dissimilar suggesting that one of these clones is a splice variant of the other.

The 5' RACE protocol was used to isolate the 5' region of the hGlcNAc-TV-b cDNA sequence. First strand cDNA synthesis was performed using a PCR primer that was incubated (primer TVB#1A—CCAGACCTGGTCG-GCCCCTGCAGCCACAG) (SEQ ID NO. 13) (100 mM final concentration) with 2 μg of mRNA from PFSK-1 cells (ATCC CRL-2060 primitive neuroectodermal tumor) and incubated for 10 minutes at 85° C. and then chilled on ice for 1 minute. To this mixture was added, to final concentrations, 20 mM Tris-HCl (pH 8.4), 50 mM KCl, 2.5 mM MgCl$_2$, 10 mM DTT, 400 μM each dATP, dCTP, dGTP, dTTP and 200 Units of Superscript II RT (GIBCO-BRL) and incubated for 50 minutes at 42° C. The reaction was terminated by placing it at 70° C. for 15 minutes which was then incubated with 2 Units of RNAse and incubated for an additional 30 minutes. The generated cDNA was purified by using GlassMax DNA spin cartridges following the manufacturer's instructions (GIBCO-BRL). The isolated cDNA was tailed with terminal deoxynucleotidyl transferase (TdT) that added homopolymeric dCTP tails to the 3' ends of the cDNA in a reaction that was incubated for 10 minutes at 37° C. with a final composition of 10 mM Tris-HCl (pH 8.4), 25 mM KCl, 1.5 mM MgCl$_2$, 200 μM dCTP and 1 Unit of TdT. The TdT was heat inactivated for 10 minutes at 65° C. The tailed cDNA (5 μl) was amplified by PCR using two primers (primer TVB#1B—GGAGGCAGCCCCGGGAGCTGGGAG (SEQ ID NO. 14) and an Abridged Anchor primer—sequence not provided from GIBCO-BRL) with the final composition of the reaction as 20 mM Tris-HCl (pH 8.4), 50 mM KCl, 1.5 mM MgCl$_2$, 400 mM primer TVB#1B, 400 mM Abridged Anchor primer, 200 μM each dATP, dCTP, dGTP, dTTP and 2.5 Units of Taq DNA polymerase. This reaction was transferred to a thermal cycler preequilibrated to 94° C. Thirty five cycles of PCR was performed with the following cycling protocol: predenaturation at 94° C. for 2 minutes, denaturation at 94° C. for 1 minute, annealing of primers at 58° C. for 1.5 minutes, primer extension at 72° C. for 2.5 minutes and final extension at 72° C. for 10 minutes. The 5' RACE products were analyzed using standard agarose gel electrophoresis protocols. No visible bands were observed therefore the region above 1.6 kb marker was isolated using a DNA gel extraction kit from Stratagene and subcloned into the T/A Bluescript vector using standard procedures. Several cDNA fragments were subcloned into the Bluescript vector and were sequenced. Only one clone containing a 1.7 kb cDNA fragment was similar to hGlcNAc-TV-b. The actual size of this cDNA fragment is 1676 base pairs which did not encompass the entire hGlcNAc-TV-b clone, therefore a second round of 5' RACE was performed using the same protocol as above with different primers. To isolate the 5' end of hGlcNAc-TV-b, another primer TVB#2A (GGTCAAGATAAATGCGTTTTTCCACCGATC) (SEQ ID NO. 15) was used in place of primer TVB#1A, and TVB#2B (GTGGATTATATCCTATGGCAGAAA-AGCTTTATAT) (SEQ ID NO. 16) was used replacing TVB#2A. This set of primers generated three cDNA fragments (3, 1.7 and 1.4 kb) which were isolated following the manufacturer's instructions using a DNA gel extraction kit from Stratagene and subcloned into the T/A Bluescript vector using standard procedures. Each of the cDNA fragments were sequenced which revealed that only the 1.4 kb fragment was similar to hGlcNAc-TV and represents the 5' end of hGlcNAc-TV-b. The actual size of this fragment is 1440 base pairs.

The entire cDNA sequence of hGlcNAc-TV-b is 4541 base pairs and was reconstructed by first isolating a 1431 base pair band (designated band A) (Stratagene gel extraction kit) from the 1440 base pair 5' end of hGTNV (from the second round of 5' RACE) by restriction enzyme digestion with HindIII. Second, the middle section of hGlcNAc-TV-b (1623 base pairs-designated band B) was isolated from the 1676 base pair hGlcNAc-TVb fragment (from the first round of 5' RACE) by restriction enzyme digestions with HindIII and SmaI and then ligated (using standard protocols) to band A. And finally the 3' end of hGTNVb was isolated by using the SmaI restriction enzyme to isolate a 1487 base pair band (designated band C). Band C was then ligated to band A+B to generate the entire nontranslated and translated sequence of hGlcNAc-TV-b.

EXAMPLE 2
Expression of GlcNAc-TV-b
Northern Blot Analysis of Human Tissues

Human multiple tissue and tumor cell line Northern blots were obtained from Clontech. The Northern blot containing mRNA from human breast and uterus cancer tissues as well as normal tissues was obtained from Invitrogen. All Northern blots contained 2 g of mRNA/lane. These blots were hybridized with [α-$^{32}$P]dCTP-labeled hGlcNAc-TV (nucleotides 1508–1921) and GlcNAc-TV-b (nucleotides 1959–2417) cDNAs. Amersham multiprime DNA labeling kit and [α-$^{32}$P]dCTP (3000 Ci/mol) were used for labeling. Northern blots were hybridized under stringent conditions following the recommended protocol (Clontech) and exposed to x-ray film or phosphoimager.

Results

Figure 2:
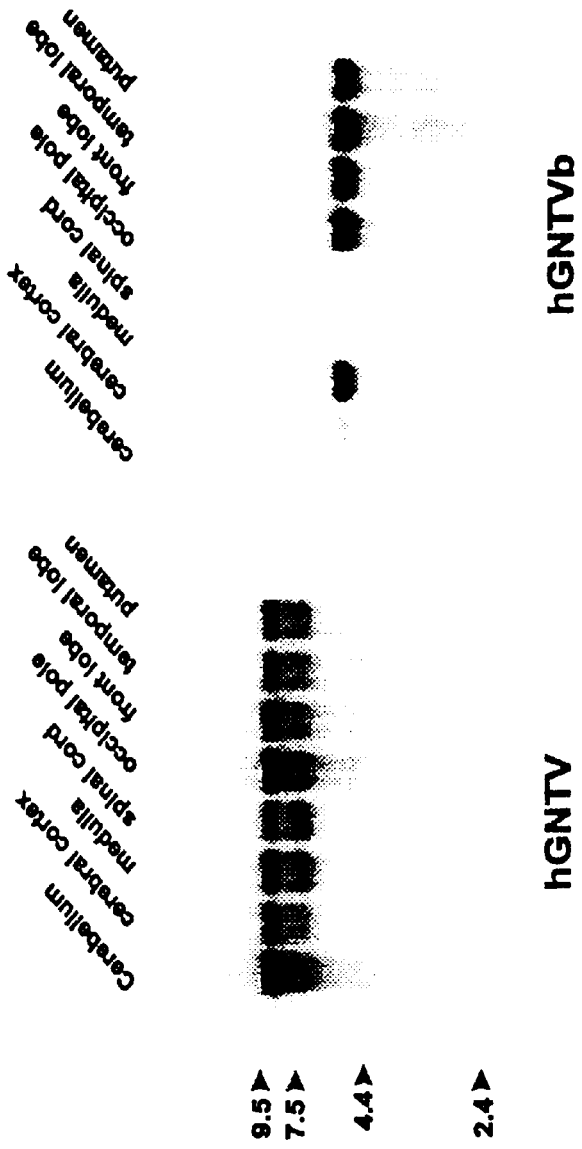
FIG. 2 is a reproduction of autoradiograms resulting from a Northern hybridization experiment in which mRNA isolated from different human brain tissues was size-fractionated and probed with radioactive human partial GlcNAc-TV clone (nucleotides 1508–1921) and human partial GlcNAc-TV-b (nucleotides 1959–2417)
Figure 3:
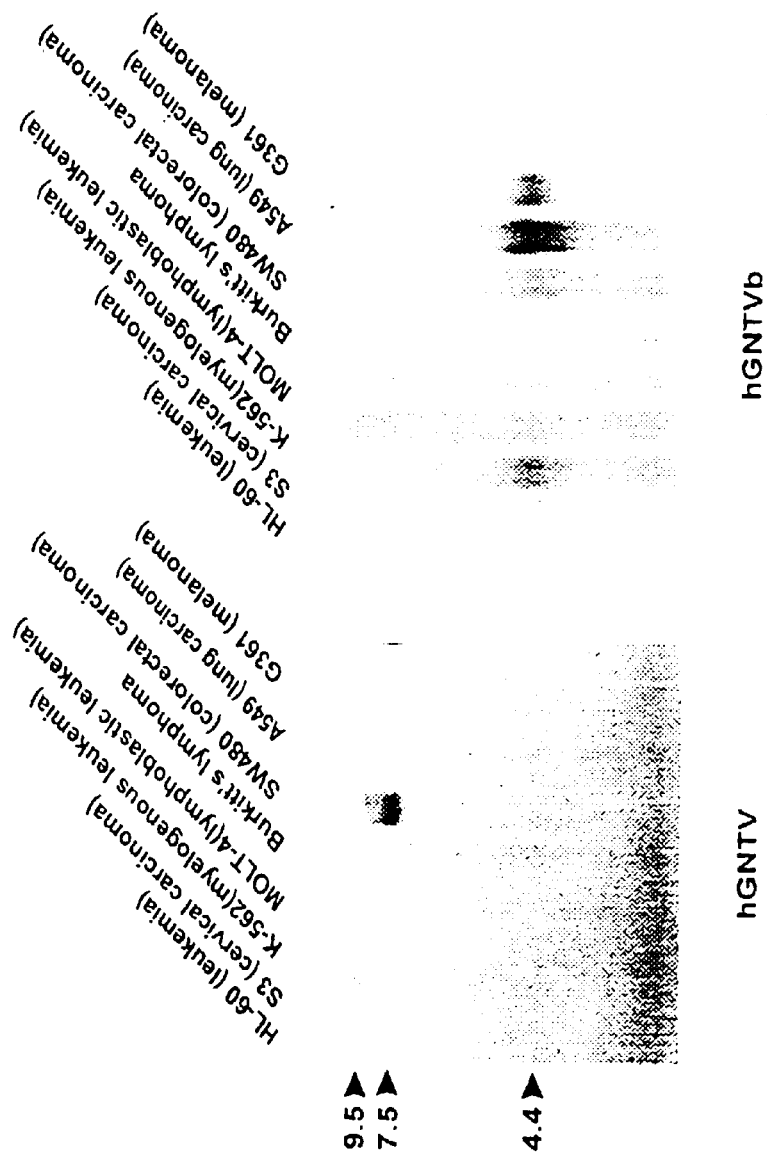
FIG. 3 is a reproduction of phosphoimager resulting from a Northern hybridization experiment in which mRNA isolated from different human tumor cell lines was size-fractionated and probed with radioactive human partial GlcNAc-TV clone (nucleotides 1508–1921) and human partial GlcNAc-TV (nucleotides 1959–2417).

The expression pattern of the two GlcNAc-TVs was examined in different human tissues. Hybridization of GlcNAc-TV cDNA probe to Northern blots under stringent conditions revealed the wide expression of two transcripts ranging in size from 7.4–9.5 kb (FIG. 1). The major transcript 9.3 kb was expressed in most tissues as well as in different parts of human brain (FIG. 2). The 9.3 kb and 7.4 kb transcripts were not detected in human tumor cell lines with the exception of human colorectal cell line SW480 (FIG. 3). Although in this case the 7.4 kb transcript was a predominant one. When the same blots were tested with GlcNAc TV-b cDNA probe, a very different pattern of tissue specific expression was observed. The high levels of 4.5 kb transcript were expressed in brain tissue and low levels in testis (FIG. 1). The presence of this transcript was not detected in other tested tissues. The GlcNAc-TV-b transcript was expressed throughout the adult brain with the exception of spinal cord (FIG. 2). Four cell lines derived from solid tumors revealed expression of GlcNAc-TVb, whereas the 4.5 kb transcript was not detected in leukemia and lymphoma (FIG. 3). The high expression of GlcNAc-TVb was detected in two different human tumor tissues (breast and uterus) whereas normal tissue, adjacent to tumor tissues showed very low levels of GlcNAc-TVb transcript.

Having illustrated and described the principles of the invention in a preferred embodiment, it should be appreciated to those skilled in the art that the invention can be modified in arrangement and detail without departure from such principles. All modifications coming within the scope of the following claims are claimed.

All publications, patents and patent applications referred to herein are incorporated by reference in their entirety to the same extent as if each individual publication, patent or patent application was specifically and individually indicated to be incorporated by reference in its entirety. Nothing herein is to be construed as an admission that the invention is not entitled to antedate such disclosures by virtue of prior invention.

We claim:

1. An isolated N-acetylglycosaminyltransferase V-b protein comprising an amino acid sequence of SEQ ID NO. 2, SEQ ID NO. 4, or SEQ ID NO. 6 or an isolated N-acetylglycosaminyltransferase V-c protein comprising an amino acid sequence of SEQ ID NO. 10 or SEQ ID NO. 12.

2. An isolated nucleic acid molecule comprising a nucleic acid sequence of SEQ ID NO. 1, SEQ ID NO. 3, SEQ ID NO. 5, SEQ ID NO. 9 or SEQ ID NO. 11.

3. An isolated nucleic acid molecule encoding a polypeptide comprising an amino acid sequence of SEQ ID NO. 2, SEQ ID NO. 4, SEQ ID NO. 6, SEQ ID NO. 10, or SEQ ID NO. 12.

4. The isolated nucleic acid molecule of claim 2, wherein the nucleic acid molecule is fused to a nucleic acid which encodes a heterologous protein.

5. A vector comprising an isolated nucleic acid molecule of claim 2.

6. A vector comprising an isolated nucleic acid molecule of claim 3.

7. A host cell comprising an isolated nucleic acid molecule of claim 2.

8. A host cell comprising an isolated nucleic acid molecule of claim 3.

9. A method for preparing a protein comprising:

(a) transferring into host cells, a vector as claimed in claim 5;
(b) selecting transformed host cells from untransformed host cells;
(c) culturing a selected transformed host cell under conditions which allow expression of the protein; and
(d) isolating the protein.

10. A method for preparing a protein comprising:
(a) transferring into host cells, a vector as claimed in claim 6;
(b) selecting transformed host cells from untransformed host cells;
(c) culturing a selected transformed host cell under conditions which allow expression of the protein; and
(d) isolating the protein.

* * * * *

SEQUENCE LISTING

<160> NUMBER OF SEQ ID NOS: 16

<210> SEQ ID NO 1
<211> LENGTH: 2061
<212> TYPE: DNA
<213> ORGANISM: Homo sapiens

<400> SEQUENCE: 1

| | | | | | | |
|---|---|---|---|---|---|---|
| atgtttttta | caatctcaag | aaaaaatatg | tcccagaaat | tgagtttact | gttgcttgta | 60 |
| tttggactca | tttggggatt | gatgttactg | cactatactt | ttcaacaacc | aagacatcaa | 120 |
| agcagtgtca | agttacgtga | gcaaatacta | gacttaagca | aaagatatgt | taaagctcta | 180 |
| gcagaggaaa | ataagaacac | agtggatgtc | gagaacggtg | cttctatggc | aggatatgcg | 240 |
| gatctgaaaa | gaacaattgc | tgtccttctg | gatgacattt | tgcaacgatt | ggtgaagctg | 300 |
| gagaacaaag | ttgactatat | tgttgtgaat | ggctcagcag | ccaacaccac | caatggtact | 360 |
| agtgggaatt | tggtgccagt | aaccacaaat | aaaagaacga | atgtctcggg | cagtatcagg | 420 |
| atagcagttg | aaaatcacct | tgtgctgctc | catccactgt | ggattatatc | ctatggcaga | 480 |
| aaagctttat | attgctggct | taggacagag | gcaatacttt | acaataaaag | cactaacgga | 540 |
| ggtcaagata | aatgcgtttt | tccaccgatc | gacggttacc | cacactacga | gggaaaaatt | 600 |
| aagtggataa | atgacatgtg | ccgttcggat | ccgtgcaagg | ctcattatgg | tatagatggg | 660 |
| tccagttgca | cttttttat | atacctcagt | gacgccgaca | atcattgtcc | ccatgcaccc | 720 |
| tggagacata | aaaatcctta | cgacgacgct | gagcataatt | catgcgctga | aattcgtagt | 780 |
| gattttgaac | ttctgtacag | tgtgattcat | cataaggacg | agttccattt | tatgagacta | 840 |
| cggagacggc | gaatggttga | gggatgggcc | caaatcgcaa | agtccctagc | agataagcag | 900 |
| aacgcagaga | agaaaaaacg | gaaaaaggcc | ctagttcacc | tgggaatcat | taccaaggac | 960 |
| actgtatcta | agattgctga | aacaggtttc | agtgccgcac | ctcttggtga | cttagttcat | 1020 |
| tggagtgatg | taattacatc | tgcgtacgca | gcggggcatg | acgttaggat | cactgcatca | 1080 |
| ctggctgagc | tcaaggatgt | cgtgaagaag | attataggta | accgatctgg | ttgcccatct | 1140 |
| gtaggagaca | gaattgttga | gctactttac | gctgatgtaa | ttggactcgg | tcaattcaag | 1200 |
| aaaactctag | gtccaacctg | ggctcaacat | cggtggatgg | ttcgagtcct | tgaaactttt | 1260 |
| ggatcagatc | ccgattttga | acatgccaat | tatgcgcaaa | caagggtca | caagagccct | 1320 |
| tggggatggt | ggaatctgaa | ccctaataac | ttttatacaa | tgttccccca | tactccagaa | 1380 |
| aacacttttc | ttgggtttgc | gatcgagcag | cacctaaact | ccagtgatat | gcaccacctt | 1440 |
| aatgagatga | agaggcagaa | tcagacgctt | gtgtatggca | agtggatag | cttctggaag | 1500 |
| aataagcata | tttacttcga | aatcattcac | aattacatcg | aagtgcaagc | aactgtgtat | 1560 |
| gactcctcta | cacccaatat | tccctcttac | tctcgaaacc | acggtattct | ttctggtcgg | 1620 |
| gaccatcgat | tcctcctccg | agagaccttc | ttgttactag | gactagggac | tccttacgaa | 1680 |
| cgttgcgctc | cgctggaagc | catggcaaat | cgatgcgtct | ttctcaaacc | gaagttcccc | 1740 |
| ccacccaatt | caaggaagaa | tacagagttt | ttacgaggca | agcccacctc | cagagaggtg | 1800 |
| ttctcccagc | atccctacgc | ggagaacttc | atcggcaagc | ccacgtgtg | acagtcgac | 1860 |
| tacaacaact | cagaggagtt | tgaagcagcc | atcaaggcca | ttatgagaac | tcaggtagac | 1920 |
| ccctacctac | cctacgagta | cacctgcgag | gggatgctgg | agcggatcac | cgcctacatc | 1980 |
| cagcaccagg | acttctgcag | agcttcagaa | cactgccacc | cacccagttt | tataatccgc | 2040 |

-continued tccctctcca gggcaacccc a                                      2061

<210> SEQ ID NO 2
<211> LENGTH: 687
<212> TYPE: PRT
<213> ORGANISM: Homo sapiens

<400> SEQUENCE: 2

```
Met Phe Phe Thr Ile Ser Arg Lys Asn Met Ser Gln Lys Leu Ser Leu
 1               5                  10                  15

Leu Leu Leu Val Phe Gly Leu Ile Trp Gly Met Leu Leu His Tyr
             20                  25                  30

Thr Phe Gln Gln Pro Arg His Gln Ser Ser Val Lys Leu Arg Glu Gln
         35                  40                  45

Ile Leu Asp Leu Ser Lys Arg Tyr Val Lys Ala Leu Ala Glu Glu Asn
 50                  55                  60

Lys Asn Thr Val Asp Val Glu Asn Gly Ala Ser Met Ala Gly Tyr Ala
 65                  70                  75                  80

Asp Leu Lys Arg Thr Ile Ala Val Leu Leu Asp Asp Ile Leu Gln Arg
                 85                  90                  95

Leu Val Lys Leu Glu Asn Lys Val Asp Tyr Ile Val Val Asn Gly Ser
                100                 105                 110

Ala Ala Asn Thr Thr Asn Gly Thr Ser Gly Asn Leu Val Pro Val Thr
            115                 120                 125

Thr Asn Lys Arg Thr Asn Val Ser Gly Ser Ile Arg Ile Ala Val Glu
        130                 135                 140

Asn His Leu Val Leu Leu His Pro Leu Trp Ile Ile Ser Tyr Gly Arg
145                 150                 155                 160

Lys Ala Leu Tyr Cys Trp Leu Arg Thr Glu Ala Ile Leu Tyr Asn Lys
                165                 170                 175

Ser Thr Asn Gly Gly Gln Asp Lys Cys Val Phe Pro Pro Ile Asp Gly
                180                 185                 190

Tyr Pro His Tyr Glu Gly Lys Ile Lys Trp Ile Asn Asp Met Cys Arg
            195                 200                 205

Ser Asp Pro Cys Lys Ala His Tyr Gly Ile Asp Gly Ser Ser Cys Thr
        210                 215                 220

Phe Phe Ile Tyr Leu Ser Asp Ala Asp Asn His Cys Pro His Ala Pro
225                 230                 235                 240

Trp Arg His Lys Asn Pro Tyr Asp Asp Ala Glu His Asn Ser Cys Ala
                245                 250                 255

Glu Ile Arg Ser Asp Phe Glu Leu Leu Tyr Ser Val Ile His His Lys
                260                 265                 270

Asp Glu Phe His Phe Met Arg Leu Arg Arg Arg Met Val Glu Gly
            275                 280                 285

Trp Ala Gln Ile Ala Lys Ser Leu Ala Asp Lys Gln Asn Ala Glu Lys
        290                 295                 300

Lys Lys Arg Lys Lys Ala Leu His Leu Gly Ile Ile Thr Lys Asp
305                 310                 315                 320

Thr Val Ser Lys Ile Ala Glu Thr Gly Phe Ser Ala Ala Pro Leu Gly
                325                 330                 335

Asp Leu Val His Trp Ser Asp Val Ile Thr Ser Ala Tyr Ala Ala Gly
            340                 345                 350

His Asp Val Arg Ile Thr Ala Ser Leu Ala Glu Leu Lys Asp Val Val
        355                 360                 365
```

```
Lys Lys Ile Ile Gly Asn Arg Ser Gly Cys Pro Ser Val Gly Asp Arg
        370                 375                 380

Ile Val Glu Leu Leu Tyr Ala Asp Val Ile Gly Leu Gly Gln Phe Lys
385                 390                 395                 400

Lys Thr Leu Gly Pro Thr Trp Ala Gln His Arg Trp Met Val Arg Val
                    405                 410                 415

Leu Glu Thr Phe Gly Ser Asp Pro Asp Phe Glu His Ala Asn Tyr Ala
                420                 425                 430

Gln Thr Lys Gly His Lys Ser Pro Trp Gly Trp Trp Asn Leu Asn Pro
            435                 440                 445

Asn Asn Phe Tyr Thr Met Phe Pro His Thr Pro Glu Asn Thr Phe Leu
        450                 455                 460

Gly Phe Ala Ile Glu Gln His Leu Asn Ser Ser Asp Met His His Leu
465                 470                 475                 480

Asn Glu Met Lys Arg Gln Asn Gln Thr Leu Val Tyr Gly Lys Val Asp
                    485                 490                 495

Ser Phe Trp Lys Asn Lys His Ile Tyr Phe Glu Ile Ile His Asn Tyr
                500                 505                 510

Ile Glu Val Gln Ala Thr Val Tyr Asp Ser Ser Thr Pro Asn Ile Pro
            515                 520                 525

Ser Tyr Ser Arg Asn His Gly Ile Leu Ser Gly Arg Asp His Arg Phe
        530                 535                 540

Leu Leu Arg Glu Thr Phe Leu Leu Leu Gly Leu Gly Thr Pro Tyr Glu
545                 550                 555                 560

Arg Cys Ala Pro Leu Glu Ala Met Ala Asn Arg Cys Val Phe Leu Lys
                    565                 570                 575

Pro Lys Phe Pro Pro Asn Ser Arg Lys Asn Thr Glu Phe Leu Arg
                580                 585                 590

Gly Lys Pro Thr Ser Arg Glu Val Phe Ser Gln His Pro Tyr Ala Glu
            595                 600                 605

Asn Phe Ile Gly Lys Pro His Val Trp Thr Val Asp Tyr Asn Asn Ser
        610                 615                 620

Glu Glu Phe Glu Ala Ala Ile Lys Ala Ile Met Arg Thr Gln Val Asp
625                 630                 635                 640

Pro Tyr Leu Pro Tyr Glu Tyr Thr Cys Glu Gly Met Leu Glu Arg Ile
                    645                 650                 655

Thr Ala Tyr Ile Gln His Gln Asp Phe Cys Arg Ala Ser Glu His Cys
                660                 665                 670

His Pro Pro Ser Phe Ile Ile Arg Ser Leu Ser Arg Ala Thr Pro
            675                 680                 685

<210> SEQ ID NO 3
<211> LENGTH: 4541
<212> TYPE: DNA
<213> ORGANISM: Homo sapiens

<400> SEQUENCE: 3
ggctcttacc gcagcctgag tttcagcagc tgctgcgcaa ggccaaactc ttcctcgggt      60
ttggcttccc ctacgagggc cccgccccc tggaggccat cgccaatggt tgcatcttcc     120
tgcagtcccg cttcagcccg ccccacagct ccctcaacca cgagttcttc ccaggcaagc     180
ccacctccag agaggtgttc tcccagcatc cctacgcgga gaacttcatc ggcaagcccc     240
acgtgtggac agtcgactac aacaactcag aggagtttga gcagccatc aaggccatta     300
```

```
tgagaactca ggtagacccc tacctaccct acgagtacac ctgcgagggg atgctggagc    360
ggatccacgc ctacatccag caccaggact tctgcagagc tccagaccac tgccctacca    420
gaggcccacg ccccgcagag ccccttttgtc ctggccccca atgccaccca cctcgagtgg    480
gctcggaaca ccagcttggc tcctggggcc tggccccgc gcacaccctg cgggcctggc    540
tggccgtgcc tgggagggcc tgcaccgaca cctgcctgga ccacgggcta atctgtgagc    600
cctccttctt cccctttcctg aacagccagg acgccttcct caagctgcag gtgccctgtg    660
acagcaccga gtcggagatg aaccaccctgt actctcggcg ttcgcccagc ctggccagga    720
gtgctacctg cagaaggagc ctctgctctt cagtgcgccg gctccaacac caagtaccgc    780
cggctctgcc cctgccgcga cttccgcaag cggaattccg gccggaattc cggaattctt    840
ttgcttttta cgagtcgagt ttttttttcctt tttttttttca agtcttgatt tgtggcttac    900
ctcaagttac cattttttcag tcaagtctgt ttgtttgctt cttcagaaat gttttttaca    960
atctcaagaa aaaatatgtc ccagaaattg agtttactgt tgcttgtatt tggactcatt   1020
tggggattga tgttactgca ctatactttt caacaaccaa gacatcaaag cagtgtcaag   1080
ttacgtgagc aaatactaga cttaagcaaa agatatgtta aagctctagc agaggaaaat   1140
aagaacacag tggatgtcga gaacggtgct tctatggcag gatatgcgga tctgaaaaga   1200
acaattgctg tccttctgga tgacatttttg caacgattgg tgaagctgga gaacaaagtt   1260
gactatattg ttgtgaatgg ctcagcagcc aacaccacca atggtactag tgggaatttg   1320
gtgccagtaa ccacaaataa aagaacgaat gtctcgggca gtatcaggat agcagttgaa   1380
aatcaccttg tgctgctcca tccactgtgg attatatcct atggcagaaa agctttatat   1440
tgctggctta ggacagaggc aatactttac aataaaagca ctaacggagg tcaagataaa   1500 tgcgttttc caccgatcga cggttaccca cactacgagg gaaaaattaa gtggataaat   1560
gacatgtgcc gttcggatcc gtgcaaggct cattatggta tagatgggtc cagttgcact   1620
ttttttatat acctcagtga cgccgacaat cattgtcccc atgcaccctg gagacataaa   1680
aatccttacg acgacgctga gcataattca tgcgctgaaa ttcgtagtga ttttgaactt   1740
ctgtacagtg tgattcatca taaggacgag ttccatttta tgagactacg gagacggcga   1800
atggttgagg gatgggccca aatcgcaaag tccctagcag ataagcagaa cgcagagaag   1860
aaaaaacgga aaaaggccct agttcacctg ggaatcatta ccaaggacac tgtatctaag   1920
attgctgaaa caggtttcag tgccgcacct cttggtgact tagttcattg gagtgatgta   1980
attacatctg cgtacgcagc ggggcatgac gttaggatca ctgcatcact ggctgagctc   2040
aaggatgtcg tgaagaagat tataggtaac cgatctggtt gcccatctgt aggagacaga   2100
attgttgagc tactttacgc tgatgtaatt ggactcggtc aattcaagaa aactctaggt   2160
ccaacctggg ctcaacatcg gtggatggtt cgagtccttg aaacttttgg atcagatccc   2220
gattttgaac atgccaatta tgcgcaaaca aagggtcaca agagcccttg gggatggtgg   2280
aatctgaacc ctaataactt ttatacaatg ttcccccata ctccagaaaa cacttttctt   2340
gggtttgcga tcgagcagca cctaaactcc agtgatatgc accaccttaa tgagatgaag   2400
aggcagaatc agacgcttgt gtatggcaaa gtggatagct tctggaagaa taagcatatt   2460
tacttcgaaa tcattcacaa ttcacatcgaa gtgcaagcaa ctgtgtatga ctcctctaca   2520
cccaatattc cctcttactc tcgaaaccac ggtattcttt ctggtcggga ccatcgattc   2580
ctcctccgag agaccttctt gttactagga ctagggactc cttacgaacg ttgcgctccg   2640
ctggaagcca tggcaaatcg atgcgtcttt ctcaaaccga agttcccccc acccaattca   2700
```

-continued

```
aggaagaata cagagttttt acgaggcaag cccacctcca gagaggtgtt ctcccagcat   2760
ccctacgcgg agaacttcat cggcaagccc cacgtgtgga cagtcgacta acaactca    2820 gaggagtttg aagcagccat caaggccatt atgagaactc aggtagaccc ctacctaccc   2880
tacgagtaca cctgcgaggg gatgctggag cggatcaccg cctacatcca gcaccaggac   2940
ttctgcagag cttcagaaca ctgccaccca cccagtttta atccgctc cctctccagg    3000 gcaaccccac ccaccagcct aggcctgctc ctccaccttc cgggaggcag ccccgggagc   3060
tgggagctgg tggaggggcc aggctggacg cttcccgtgg gagtcccctc cagacctggt   3120
cggcccctgc agccacagaa ccacgatggc aaaaaatcta tttgttctca aggactaacc   3180
tttgggggga aagcaataga gacactcttt ttctctcttt ttttaaagat ttatttcttt   3240
aaataataaa tattttattt ggatgtgagg tgcagaagag aaaaaaaaaa aaaaaaaaa    3300 aagcgcggcc gcaagcttat tccctttagt gagggttaat ttaaaagca aaagaattcc   3360 ggcctgagct cagctaggac agtgactatt aatatagtt aatgccagga actttcaccc   3420
cacgtatgga agagttcaat cttagagtag acaccttgtg aatacacaaa ccaacactcc   3480
cttctgaatt ctcattccta gcacattgtc cttacagatt cccagggggac accaagaggt   3540 ttttgcctat ataaaattaa ctagcaacag taaatggtga agtcctaatt aaataagcat   3600
gggttaaaag ccagtcgtct gctaagatgg tgaagggtgt ccccatcccc atgtttaata   3660
aatgattgct gaatccacaa ttcctctaaa gttgatggga aagtttccat ctttcagata   3720
agagcatatt atcaacggtt aaggatatc ccaggccctc cagcaaatgc cttctggaat   3780
catctccaca ttcagacaca tcgtaaacaa cagagggca atactcatgc ttcgcaaaag   3840
ccgttcattc cccttggcaa aggcgggaga gagggctcac caaccttgga gaagcctggt   3900
ttacatcgtc aaggtagcta ctgccctcta gtgttgatat gggaataaag caaaaaagta   3960
tacctggttg aaacgaaacc gaactccaca agttttttca attactgatg tgtctcagca   4020
gccttggtag gagcttggaa acatcatca ggtgaggata ttgcactgga gctgacctct   4080
tgtggcttct aaagtttctt tttttttttt tttttttttt tgagacagag tctcactgtg   4140
tcacccaggc tggagtgcat tttcttgtgt ccaaccaaga ctcacatacc atctcagctc   4200
actgcaacct ccacctccca ggttcaagag atgctcctgc cctagcctcc caagtagctg   4260
ggatcacagg catgtgccac cacacccagc taagttttgt attttagaa gagatggggt   4320 ttcacgatgt tggccagact ggtctcgaac tcctgaccta aagtgatcca cctgccttgg   4380
cttcccaaaa tgctggatta caggtgtgaa ccactgcacc tggcctccaa gatttctatt   4440
tggcaaattc acatagctac tttcatactt gttaaaatac cgaaatgctt ccataccagt   4500
tagcaaaagg ccacccggaa ttcagcttgg acttaaccag g                      4541
```

<210> SEQ ID NO 4
<211> LENGTH: 1485
<212> TYPE: PRT
<213> ORGANISM: Homo sapiens

<400> SEQUENCE: 4

```
Gly Ser Tyr Arg Ser Leu Ser Phe Ser Ser Cys Cys Ala Arg Pro Asn
 1               5                  10                  15

Ser Ser Ser Gly Leu Ala Ser Pro Thr Arg Ala Pro Pro Trp Arg
            20                  25                  30

Pro Ser Pro Met Val Ala Ser Ser Cys Ser Pro Ala Ser Ala Arg Pro
        35                  40                  45
```

-continued

```
Thr Ala Pro Ser Thr Thr Ser Ser Gln Ala Ser Pro Pro Glu
     50                  55                  60

Arg Cys Ser Pro Ser Ile Pro Thr Arg Thr Ser Ser Ala Ser Pro
 65                  70                  75                  80

Thr Cys Gly Gln Ser Thr Thr Thr Gln Arg Ser Leu Lys Gln Pro
                     85                  90                  95

Ser Arg Pro Leu Glu Leu Arg Thr Pro Thr Tyr Pro Thr Ser Thr Pro
                100                 105                 110

Ala Arg Gly Cys Trp Ser Gly Ser Thr Pro Thr Ser Ser Thr Arg Thr
                115                 120                 125

Ser Ala Glu Leu Gln Thr Thr Ala Leu Pro Glu Ala His Ala Pro Gln
    130                 135                 140

Ser Pro Phe Val Leu Ala Pro Asn Ala Thr His Leu Glu Trp Ala Arg
145                 150                 155                 160

Asn Thr Ser Leu Ala Pro Gly Ala Trp Pro Pro Arg Thr Pro Cys Gly
                    165                 170                 175

Pro Gly Trp Pro Cys Leu Gly Gly Pro Ala Pro Thr Pro Ala Trp Thr
                180                 185                 190

Thr Gly Ser Val Ser Pro Pro Ser Ser Pro Ser Thr Ala Arg Thr Pro
                195                 200                 205

Ser Ser Ser Cys Arg Cys Pro Val Thr Ala Pro Ser Arg Arg Thr Thr
    210                 215                 220

Cys Thr Leu Gly Val Arg Pro Ala Trp Pro Gly Val Leu Pro Ala Glu
225                 230                 235                 240

Gly Ala Ser Ala Leu Gln Cys Ala Gly Ser Asn Thr Lys Tyr Arg Arg
                    245                 250                 255

Leu Cys Pro Cys Arg Asp Phe Arg Lys Arg Asn Ser Gly Arg Asn Ser
                260                 265                 270

Gly Ile Leu Leu Leu Phe Thr Ser Arg Val Phe Phe Leu Phe Phe Phe
                275                 280                 285

Lys Ser Phe Val Ala Tyr Leu Lys Leu Pro Phe Phe Ser Gln Val Cys
    290                 295                 300

Leu Phe Ala Ser Ser Glu Met Phe Phe Thr Ile Ser Arg Lys Asn Met
305                 310                 315                 320

Ser Gln Lys Leu Ser Leu Leu Leu Val Phe Gly Leu Ile Trp Gly
                    325                 330                 335

Leu Met Leu Leu His Tyr Thr Phe Gln Gln Pro Arg His Gln Ser Ser
                340                 345                 350

Val Lys Leu Arg Glu Gln Ile Leu Asp Leu Ser Lys Arg Tyr Val Lys
    355                 360                 365

Ala Leu Ala Glu Glu Asn Lys Asn Thr Val Asp Val Glu Asn Gly Ala
    370                 375                 380

Ser Met Ala Gly Tyr Ala Asp Leu Lys Arg Thr Ile Ala Val Leu Leu
385                 390                 395                 400

Asp Asp Ile Leu Gln Arg Leu Val Lys Leu Glu Asn Lys Val Asp Tyr
                405                 410                 415

Ile Val Val Asn Gly Ser Ala Ala Asn Thr Thr Asn Gly Thr Ser Gly
                420                 425                 430

Asn Leu Val Pro Val Thr Thr Asn Lys Arg Thr Asn Val Ser Gly Ser
                435                 440                 445

Ile Arg Ile Ala Val Glu Asn His Leu Val Leu Leu His Pro Leu Trp
450                 455                 460
```

-continued

```
Ile Ile Ser Tyr Gly Arg Lys Ala Leu Tyr Cys Trp Leu Arg Thr Glu
465                 470                 475                 480

Ala Ile Leu Tyr Asn Lys Ser Thr Asn Gly Gly Gln Asp Lys Cys Val
                485                 490                 495

Phe Pro Pro Ile Asp Gly Tyr Pro His Tyr Glu Gly Lys Ile Lys Trp
            500                 505                 510

Ile Asn Asp Met Cys Arg Ser Asp Pro Cys Lys Ala His Tyr Gly Ile
            515                 520                 525

Asp Gly Ser Ser Cys Thr Phe Phe Ile Tyr Leu Ser Asp Ala Asp Asn
        530                 535                 540

His Cys Pro His Ala Pro Trp Arg His Lys Asn Pro Tyr Asp Asp Ala
545                 550                 555                 560

Glu His Asn Ser Cys Ala Glu Ile Arg Ser Asp Phe Glu Leu Leu Tyr
                565                 570                 575

Ser Val Ile His His Lys Asp Glu Phe His Phe Met Arg Leu Arg Arg
            580                 585                 590

Arg Arg Met Val Glu Gly Trp Ala Gln Ile Ala Lys Ser Leu Ala Asp
        595                 600                 605

Lys Gln Asn Ala Glu Lys Lys Arg Lys Lys Ala Leu Val His Leu
610                 615                 620

Gly Ile Ile Thr Lys Asp Thr Val Ser Lys Ile Ala Glu Thr Gly Phe
625                 630                 635                 640

Ser Ala Ala Pro Leu Gly Asp Leu Val His Trp Ser Asp Val Ile Thr
                645                 650                 655

Ser Ala Tyr Ala Ala Gly His Asp Val Arg Ile Thr Ala Ser Leu Ala
            660                 665                 670

Glu Leu Lys Asp Val Val Lys Lys Ile Ile Gly Asn Arg Ser Gly Cys
        675                 680                 685

Pro Ser Val Gly Asp Arg Ile Val Glu Leu Leu Tyr Ala Asp Val Ile
690                 695                 700

Gly Leu Gly Gln Phe Lys Lys Thr Leu Gly Pro Thr Trp Ala Gln His
705                 710                 715                 720

Arg Trp Met Val Arg Val Leu Glu Thr Phe Gly Ser Asp Pro Asp Phe
                725                 730                 735

Glu His Ala Asn Tyr Ala Gln Thr Lys Gly His Lys Ser Pro Trp Gly
            740                 745                 750

Trp Trp Asn Leu Asn Pro Asn Asn Phe Tyr Thr Met Phe Pro His Thr
        755                 760                 765

Pro Glu Asn Thr Phe Leu Gly Phe Ala Ile Glu Gln His Leu Asn Ser
770                 775                 780

Ser Asp Met His His Leu Asn Glu Met Lys Arg Gln Asn Gln Thr Leu
785                 790                 795                 800

Val Tyr Gly Lys Val Asp Ser Phe Trp Lys Asn Lys His Ile Tyr Phe
                805                 810                 815

Glu Ile Ile His Asn Tyr Ile Glu Val Gln Ala Thr Val Tyr Asp Ser
            820                 825                 830

Ser Thr Pro Asn Ile Pro Ser Tyr Ser Arg Asn His Gly Ile Leu Ser
        835                 840                 845

Gly Arg Asp His Arg Phe Leu Leu Arg Glu Thr Phe Leu Leu Leu Gly
850                 855                 860

Leu Gly Thr Pro Tyr Glu Arg Cys Ala Pro Leu Glu Ala Met Ala Asn
865                 870                 875                 880

Arg Cys Val Phe Leu Lys Pro Lys Phe Pro Pro Asn Ser Arg Lys
```

-continued

```
                885                 890                 895
Asn Thr Glu Phe Leu Arg Gly Lys Pro Thr Ser Arg Glu Val Phe Ser
            900                 905                 910
Gln His Pro Tyr Ala Glu Asn Phe Ile Gly Lys Pro His Val Trp Thr
            915                 920                 925
Val Asp Tyr Asn Asn Ser Glu Glu Phe Glu Ala Ala Ile Lys Ala Ile
            930                 935                 940
Met Arg Thr Gln Val Asp Pro Tyr Leu Pro Tyr Glu Tyr Thr Cys Glu
945                 950                 955                 960
Gly Met Leu Glu Arg Ile Thr Ala Tyr Ile Gln His Gln Asp Phe Cys
            965                 970                 975
Arg Ala Ser Glu His Cys His Pro Pro Ser Phe Ile Ile Arg Ser Leu
            980                 985                 990
Ser Arg Ala Thr Pro Pro Thr Ser Leu Gly Leu Leu Leu His Leu Pro
            995                 1000                1005
Gly Gly Ser Pro Gly Ser Trp Glu Leu Val Glu Gly Pro Gly Trp Thr
            1010                1015                1020
Leu Pro Val Gly Val Pro Ser Arg Pro Gly Arg Pro Leu Gln Pro Gln
1025                1030                1035                1040
Asn His Asp Gly Lys Lys Ser Ile Cys Ser Gln Gly Leu Thr Phe Gly
            1045                1050                1055
Gly Lys Ala Ile Glu Thr Leu Phe Phe Ser Leu Phe Leu Lys Ile Tyr
            1060                1065                1070
Phe Phe Lys Ile Phe Tyr Leu Asp Val Arg Cys Arg Arg Glu Lys Lys
            1075                1080                1085
Lys Lys Lys Lys Lys Arg Gly Arg Lys Leu Ile Pro Phe Ser Glu Gly
            1090                1095                1100
Phe Lys Lys Gln Lys Asn Ser Gly Leu Ser Ser Ala Arg Thr Val Thr
1105                1110                1115                1120
Ile Tyr Ser Cys Gln Glu Leu Ser Pro His Val Trp Lys Ser Ser Ile
            1125                1130                1135
Leu Glu Thr Pro Cys Glu Tyr Thr Asn Gln His Ser Leu Leu Asn Ser
            1140                1145                1150
His Ser His Ile Val Leu Thr Asp Ser Gln Gly Thr Pro Arg Gly Phe
            1155                1160                1165
Cys Leu Tyr Lys Ile Asn Gln Gln Met Val Lys Ser Leu Asn Lys His
            1170                1175                1180
Gly Leu Lys Ala Ser Arg Leu Leu Arg Trp Arg Val Ser Pro Ser Pro
1185                1190                1195                1200
Cys Leu Ile Asn Asp Cys Ile His Asn Ser Ser Lys Val Asp Gly Lys
            1205                1210                1215
Val Ser Ile Phe Gln Ile Arg Ala Tyr Tyr Gln Arg Leu Lys Asp Ile
            1220                1225                1230
Pro Gly Pro Pro Ala Asn Ala Phe Trp Asn His Leu His Ile Gln Thr
            1235                1240                1245
His Arg Lys Gln Gln Arg Gly Asn Thr His Ala Ser Gln Lys Pro Phe
            1250                1255                1260
Ile Pro Leu Gly Lys Gly Gly Arg Glu Gly Ser Pro Thr Leu Glu Lys
1265                1270                1275                1280
Pro Gly Leu His Arg Gln Gly Ser Tyr Cys Pro Leu Val Leu Ile Trp
            1285                1290                1295
Glu Ser Lys Lys Val Tyr Leu Val Glu Thr Lys Pro Asn Ser Thr Lys
            1300                1305                1310
```

-continued

Phe Phe Asn Tyr Cys Val Ser Ala Ala Leu Val Gly Ala Trp Lys Thr
1315                1320                1325

Ser Ser Gly Glu Asp Ile Ala Leu Glu Leu Thr Ser Cys Gly Phe Ser
    1330                1335                1340

Phe Phe Phe Phe Phe Phe Phe Phe Leu Arg Gln Ser Leu Thr Val Ser
1345                1350                1355                1360

Pro Arg Leu Glu Cys Ile Phe Leu Cys Pro Thr Lys Thr His Ile Pro
            1365                1370                1375

Ser Gln Leu Thr Ala Thr Ser Thr Ser Gln Val Gln Glu Met Leu Leu
        1380                1385                1390

Pro Pro Pro Lys Leu Gly Ser Gln Ala Cys Ala Thr Thr Pro Ser Val
    1395                1400                1405

Leu Tyr Phe Lys Arg Trp Gly Phe Thr Met Leu Ala Arg Leu Val Ser
    1410                1415                1420

Asn Ser Pro Lys Val Ile His Leu Pro Trp Leu Pro Lys Met Leu Asp
1425                1430                1435                1440

Tyr Arg Cys Glu Pro Leu His Leu Ala Ser Lys Ile Ser Ile Trp Gln
            1445                1450                1455

Ile His Ile Ala Thr Phe Ile Leu Val Lys Ile Pro Lys Cys Phe His
        1460                1465                1470

Thr Ser Gln Lys Ala Thr Arg Asn Ser Ala Trp Thr Pro
    1475                1480                1485

<210> SEQ ID NO 5
<211> LENGTH: 2298
<212> TYPE: DNA
<213> ORGANISM: Homo sapiens

<400> SEQUENCE: 5

```
atgttttta caatctcaag aaaaaatatg tcccagaaat tgagtttact gttgcttgta      60
tttggactca tttggggatt gatgttactg cactatactt tcaacaacc aagacatcaa     120
agcagtgtca agttacgtga gcaaatacta gacttaagca aaagatatgt taaagctcta    180
gcagaggaaa ataagaacac agtggatgtc gagaacggtg cttctatggc aggatatgcg    240
gatctgaaaa gaacaattgc tgtccttctg gatgacattt tgcaacgatt ggtgaagctg    300
gagaacaaag ttgactatat tgttgtgaat ggctcagcag ccaacaccac caatggtact    360
agtgggaatt tggtgccagt aaccacaaat aaaagaacga atgtctcggg cagtatcagg    420
atagcagttg aaaatcacct tgtgctgctc catccactgt ggattatatc ctatggcaga    480
aaagctttat attgctggct taggacagag gcaatacttt acaataaaag cactaacgga    540
ggtcaagata aatgcgtttt tccaccgatc gacggttacc cacactacga gggaaaaatt    600
aagtggataa atgacatgtg ccgttcggat ccgtgcaagg ctcattatgg tatagatggg    660
tccagttgca ctttttttat atacctcagt gacgccgaca atcattgtcc ccatgcaccc    720
tggagacata aaaatcctta cgacgacgct gagcataatt catgcgctga attcgtagt    780
gatttttgaac ttctgtacag tgtgattcat cataaggacg agttccattt tatgagacta    840
cggagacggc gaatggttga gggatgggcc caaatcgcaa agtccctagc agataagcag    900
aacgcagaga agaaaaaacg gaaaaaggcc ctagttcacc tgggaatcat taccaaggac    960
actgtatcta agattgctga acaggtttc agtgccgcac ctcttggtga cttagttcat   1020
tggagtgatg taattacatc tgcgtacgca gcgggggcatg acgttaggat cactgcatca   1080
ctggctgagc tcaaggatgt cgtgaagaag attataggta accgatctgg ttgcccatct   1140
```

```
gtaggagaca gaattgttga gctactttac gctgatgtaa ttggactcgg tcaattcaag    1200
aaaactctag gtccaacctg gctcaacat cggtggatgg ttcgagtcct tgaaactttt    1260
ggatcagatc ccgattttga acatgccaat tatgcgcaaa caaagggtca aagagccct    1320 tggggatggt ggaatctgaa ccctaataac ttttatacaa tgttccccca tactccagaa    1380 aacactttc ttgggtttgc gatcgagcag cacctaaact ccagtgatat gcaccacctt    1440
aatgagatga agaggcagaa tcagacgctt gtgtatggca aagtggatag cttctggaag    1500
aataagcata tttacttcga aatcattcac aattacatcg aagtgcaagc aactgtgtat    1560
gactcctcta cacccaatat tccctcttac tctcgaaacc acggtattct ttctggtcgg    1620
gaccatcgat tcctcctccg agagaccttc ttgttactag gactagggac tccttacgaa    1680
cgttgcgctc cgctggaagc catggcaaat cgatgcgtct ttctcaaacc gaagttcccc    1740
ccacccaatt caaggaagaa tacagagttt ttacgaggca gcccacctc cagagaggtg    1800 ttctcccagc atccctacgc ggagaacttc atcggcaagc ccacgtgtg gacagtcgac    1860 tacaacaact cagaggagtt tgaagcagcc atcaaggcca ttatgagaac tcaggtagac    1920
ccctacctac cctacgagta cacctgcgag gggatgctgg agcggatcac cgcctacatc    1980
cagcaccagg acttctgcag agcttcagaa cactgccacc cacccagttt tataatccgc    2040
tccctctcca gggcaacccc acccaccagc ctaggcctgc cctccacct tccgggaggc    2100 agccccggga gctgggagct ggtggagggg ccaggctgga cgcttcccgt gggagtcccc    2160
tccagacctg gtcggcccct gcagccacag aaccacgatg gcaaaaaatc tatttgttct    2220
caaggactaa cctttggggg gaaagcaata gagacactct ttttctctct ttttttaaag    2280
atttatttct ttaaataa                                                  2298
```

<210> SEQ ID NO 6
<211> LENGTH: 765
<212> TYPE: PRT
<213> ORGANISM: Homo sapiens

<400> SEQUENCE: 6

```
Met Phe Phe Thr Ile Ser Arg Lys Asn Met Ser Gln Lys Leu Ser Leu
 1               5                  10                  15

Leu Leu Leu Val Phe Gly Leu Ile Trp Gly Leu Met Leu His Tyr
                20                  25                  30

Thr Phe Gln Gln Pro Arg His Gln Ser Ser Val Lys Leu Arg Glu Gln
             35                  40                  45

Ile Leu Asp Leu Ser Lys Arg Tyr Val Lys Ala Leu Ala Glu Glu Asn
         50                  55                  60

Lys Asn Thr Val Asp Val Glu Asn Gly Ala Ser Met Ala Gly Tyr Ala
 65                  70                  75                  80

Asp Leu Lys Arg Thr Ile Ala Val Leu Leu Asp Asp Ile Leu Gln Arg
                 85                  90                  95

Leu Val Lys Leu Glu Asn Lys Val Asp Tyr Ile Val Asn Gly Ser
            100                 105                 110

Ala Ala Asn Thr Thr Asn Gly Thr Ser Gly Asn Leu Val Pro Val Thr
        115                 120                 125

Thr Asn Lys Arg Thr Asn Val Ser Gly Ser Ile Arg Ile Ala Val Glu
    130                 135                 140

Asn His Leu Val Leu Leu His Pro Leu Trp Ile Ile Ser Tyr Gly Arg
145                 150                 155                 160
```

-continued

```
Lys Ala Leu Tyr Cys Trp Leu Arg Thr Glu Ala Ile Leu Tyr Asn Lys
                165                 170                 175
Ser Thr Asn Gly Gly Gln Asp Lys Cys Val Phe Pro Pro Ile Asp Gly
            180                 185                 190
Tyr Pro His Tyr Glu Gly Lys Ile Lys Trp Ile Asn Asp Met Cys Arg
        195                 200                 205
Ser Asp Pro Cys Lys Ala His Tyr Gly Ile Asp Gly Ser Ser Cys Thr
210                 215                 220
Phe Phe Ile Tyr Leu Ser Asp Ala Asp Asn His Cys Pro His Ala Pro
225                 230                 235                 240
Trp Arg His Lys Asn Pro Tyr Asp Asp Ala Glu His Asn Ser Cys Ala
                245                 250                 255
Glu Ile Arg Ser Asp Phe Glu Leu Leu Tyr Ser Val Ile His His Lys
            260                 265                 270
Asp Glu Phe His Phe Met Arg Leu Arg Arg Arg Met Val Glu Gly
        275                 280                 285
Trp Ala Gln Ile Ala Lys Ser Leu Ala Asp Lys Gln Asn Ala Glu Lys
290                 295                 300
Lys Lys Arg Lys Lys Ala Leu Val His Leu Gly Ile Ile Thr Lys Asp
305                 310                 315                 320
Thr Val Ser Lys Ile Ala Glu Thr Gly Phe Ser Ala Ala Pro Leu Gly
                325                 330                 335
Asp Leu Val His Trp Ser Asp Val Ile Thr Ser Ala Tyr Ala Ala Gly
            340                 345                 350
His Asp Val Arg Ile Thr Ala Ser Leu Ala Glu Leu Lys Asp Val Val
        355                 360                 365
Lys Lys Ile Ile Gly Asn Arg Ser Gly Cys Pro Ser Val Gly Asp Arg
370                 375                 380
Ile Val Glu Leu Leu Tyr Ala Asp Val Ile Gly Leu Gly Gln Phe Lys
385                 390                 395                 400
Lys Thr Leu Gly Pro Thr Trp Ala Gln His Arg Trp Met Val Arg Val
                405                 410                 415
Leu Glu Thr Phe Gly Ser Asp Pro Asp Phe Glu His Ala Asn Tyr Ala
            420                 425                 430
Gln Thr Lys Gly His Lys Ser Pro Trp Gly Trp Trp Asn Leu Asn Pro
        435                 440                 445
Asn Asn Phe Tyr Thr Met Phe Pro His Thr Pro Glu Asn Thr Phe Leu
450                 455                 460
Gly Phe Ala Ile Glu Gln His Leu Asn Ser Ser Asp Met His His Leu
465                 470                 475                 480
Asn Glu Met Lys Arg Gln Asn Gln Thr Leu Val Tyr Gly Lys Val Asp
                485                 490                 495
Ser Phe Trp Lys Asn Lys His Ile Tyr Phe Glu Ile His Asn Tyr
            500                 505                 510
Ile Glu Val Gln Ala Thr Val Tyr Asp Ser Ser Thr Pro Asn Ile Pro
        515                 520                 525
Ser Tyr Ser Arg Asn His Gly Ile Leu Ser Gly Arg Asp His Arg Phe
530                 535                 540
Leu Leu Arg Glu Thr Phe Leu Leu Gly Leu Gly Thr Pro Tyr Glu
545                 550                 555                 560
Arg Cys Ala Pro Leu Glu Ala Met Ala Asn Arg Cys Val Phe Leu Lys
                565                 570                 575
Pro Lys Phe Pro Pro Pro Asn Ser Arg Lys Asn Thr Glu Phe Leu Arg
```

-continued

```
                580                 585                 590
Gly Lys Pro Thr Ser Arg Glu Val Phe Ser Gln His Pro Tyr Ala Glu
            595                 600                 605

Asn Phe Ile Gly Lys Pro His Val Trp Thr Val Asp Tyr Asn Asn Ser
610                 615                 620

Glu Glu Phe Glu Ala Ala Ile Lys Ala Ile Met Arg Thr Gln Val Asp
625                 630                 635                 640

Pro Tyr Leu Pro Tyr Glu Tyr Thr Cys Glu Gly Met Leu Glu Arg Ile
                645                 650                 655

Thr Ala Tyr Ile Gln His Gln Asp Phe Cys Arg Ala Ser Glu His Cys
            660                 665                 670

His Pro Pro Ser Phe Ile Ile Arg Ser Leu Ser Arg Ala Thr Pro Pro
            675                 680                 685

Thr Ser Leu Gly Leu Leu Leu His Leu Pro Gly Gly Ser Pro Gly Ser
690                 695                 700

Trp Glu Leu Val Glu Pro Gly Trp Thr Leu Pro Val Gly Val Pro
705                 710                 715                 720

Ser Arg Pro Gly Arg Pro Leu Gln Pro Gln Asn His Asp Gly Lys Lys
                725                 730                 735

Ser Ile Cys Ser Gln Gly Leu Thr Phe Gly Gly Lys Ala Ile Glu Thr
            740                 745                 750

Leu Phe Phe Ser Leu Phe Leu Lys Ile Tyr Phe Phe Lys
            755                 760                 765
```

<210> SEQ ID NO 7
<211> LENGTH: 948
<212> TYPE: DNA
<213> ORGANISM: Homo sapiens

<400> SEQUENCE: 7

```
cggctcttac cgcagcctga gtttcagcag ctgctgcgca aggccaaact cttcctcggg      60
tttggcttcc cctacgaggg ccccgccccc ctggaggcca tcgccaatgg ttgcatcttc     120
ctgcagtccc gcttcagccc gccccacagc tccctcaacc acgagttctt cccaggcaag     180
cccacctcca gagaggtgtt ctcccagcat ccctacgcgg agaacttcat cggcaagccc     240
cacgtgtgga cagtcgacta caacaactca gaggagtttg aagcagccat caaggccatt     300
atgagaactc aggtagaccc ctacctaccc tacgagtaca cctgcgaggg gatgctggag     360
cggatccacg cctacatcca gcaccaggac ttctgcagag ctccagacca ctgccctacc     420
agaggcccac gccccgcaga gccccttttgt cctggcccc aatgccaccc acctcgagtg     480
ggctcggaac accagcttgg ctcctggggc ctggccccg cgcacaccct gcgggcctgg     540
ctggccgtgc ctgggagggc ctgcaccgac acctgcctgg accacgggct aatctgtgag     600
ccctccttct tccccttcct gaacagccag gacgccttcc tcaagctgca ggtgccctgt     660
gacagcaccg agtcggagat gaaccacctg tactctcggc gttcgcccag cctggccagg     720
agtgctacct gcagaaggag cctctgctct tcagtgcgcc ggctccaaca ccaagtaccg     780
ccggctctgc ccctgccgcg acttccgcaa gcggaattcc ggccggaatt ccggaattct     840
tttgcttttt acgagtcgag ttttttttct tttttttttc aagtcttgat tgtggctta     900
cctcaagtta ccatttttca gtcaagtctg tttgtttgct tcttcaga                 948
```

<210> SEQ ID NO 8
<211> LENGTH: 1295
<212> TYPE: DNA

<213> ORGANISM: Homo sapiens

<400> SEQUENCE: 8

```
taaatatttt atttggatgt gaggtgcaga agagaaaaaa aaaaaaaaaa aaaaaagcgc      60
ggccgcaagc ttattccctt tagtgagggt taatttaaaa agcaaaagaa ttccggcctg     120
agctcagcta ggacagtgac tatttaatat agttaatgcc aggaactttc accccacgta     180
tggaagagtt caatcttaga gtagacacct tgtgaataca caaaccaaca ctcccttctg     240
aattctcatt cctagcacat tgtccttaca gattcccagg ggacaccaag aggttttgc      300
ctatataaaa ttaactagca acagtaaatg gtgaagtcct aattaaataa gcatgggtta     360
aaagccagtc gtctgctaag atggtgaagg gtgtccccat ccccatgttt aataaatgat     420
tgctgaatcc acaattcctc taagttgat gggaaagttt ccatctttca gataagagca      480
tattatcaac ggttaaagga tatcccaggc cctccagcaa atgccttctg gaatcatctc     540
cacattcaga cacatcgtaa acaacagagg gcaatactc atgcttcgca aaagccgttc      600
attcccttg gcaaaggcgg gagagagggc tcaccaacct tggagaagcc tggtttacat      660
cgtcaaggta gctactgccc tctagtgttg atatgggaat aaagcaaaaa agtatacctg     720
gttgaaacga aaccgaactc cacaaagttt ttcaattact gatgtgtctc agcagccttg     780
gtaggagctt ggaaaacatc atcaggtgag gatattgcac tggagctgac ctcttgtggc     840
ttctaaagtt tctttttttt ttttttttt ttttttgagac agagtctcac tgtgtcaccc     900
aggctggagt gcattttctt gtgtccaacc aagactcaca taccatctca gctcactgca     960
acctccacct cccaggttca agagatgctc ctgccctagc ctcccaagta gctgggatca    1020
caggcatgtg ccaccacacc cagctaagtt ttgtattttt agaagagatg gggtttcacg    1080
atgttggcca gactggtctc gaactcctga cctaaagtga tccacctgcc ttggcttccc    1140
aaaatgctgg attacaggtg tgaaccactg cacctggcct ccaagatttc tatttggcaa    1200
attcacatag ctactttcat acttgttaaa ataccgaaat gcttccatac cagttagcaa    1260
aaggccaccc ggaattcagc ttggacttaa ccagg                                1295
```

<210> SEQ ID NO 9
<211> LENGTH: 2298
<212> TYPE: DNA
<213> ORGANISM: Homo sapiens

<400> SEQUENCE: 9

```
atgttttta caatctcaag aaaaaatatg tcccagaaat tgagtttact gttgcttgta      60
tttggactca tttggggatt gatgttactg cactatactt tcaacaacc aagacatcaa      120
agcagtgtca agttacgtga gcaaatacta gacttaagca aaagatatgt taagctcta     180
gcagaggaaa ataagaacac agtggatgtc gagaacggtg cttctatggc aggatatgcg    240
gatctgaaaa gaacaattgc tgtccttctg atgacatttt gcaacgatt ggtgaagctg      300
gagaacaaag ttgactatat tgttgtgaat ggctcagcag ccaacaccac caatggtact     360
agtgggaatt tggtgccagt aaccacaaat aaaagaacga atgtctcggg cagtatcagg    420
atagcagttg aaaatcacct tgtgctgctc catccactgt ggattatatc ctatggcaga    480
aaagctttat attgctggct taggacagag gcaatacttt acaataaaag cactaacgga    540
ggtcaagata aatgcgtttt ccaccgatc gacggttacc cacactacga gggaaaaatt     600
aagtggataa atgacatgtg ccgttcggat ccgtgcaagg ctcattatgg tatagatggg    660
tccagttgca ctttttttat ataccctcagt gacgccgaca atcattgtcc ccatgcaccc    720
```

```
tggagacata aaaatcctta cgacgacgct gagcataatt catgcgctga aattcgtagt    780
gattttgaac ttctgtacag tgtgattcat cataaggacg agttccattt tatgagacta    840
cggagacggc gaatggttga gggatgggcc caaatcgcaa agtccctagc agataagcag    900
aacgcagaga agaaaaaacg gaaaaaggcc ctagttcacc tgggaatcat taccaaggac    960
actgtatcta agattgctga acaggtttca gtgccgcac ctcttggtga cttagttcat    1020
tggagtgatg taattacatc tgcgtacgca gcggggcatg acgttaggat cactgcatca    1080
ctggctgagc tcaaggatgt cgtgaagaag attataggta accgatctgg ttgcccatct    1140
gtaggagaca gaattgttga gctactttac gctgatgtaa ttggactcgg tcaattcaag    1200
aaaactctag gtccaacctg ggctcaacat cggtggatgg ttcgagtcct tgaaactttt    1260
ggatcagatc ccgattttga acatgccaat tatgcgcaaa caaagggtca aagagccct    1320 tggggatggt ggaatctgaa ccctaataac ttttatacaa tgttccccca tactccagaa    1380 aacactttc ttgggtttgc gatcgagcag caccctaaact ccagtgatat gcaccacctt    1440
aatgagatga agaggcagaa tcagacgctt gtgtatggca agtggatag cttctggaag    1500 aataagcata tttacttcga aatcattcac aattacatcg aagtgcaagc aactgtgtat    1560
gactcctcta cacccaatat tccctcttac tctcgaaacc acggtattct ttctggtcgg    1620
gaccatcgat tcctcctccg agagaccttc ttgttactag gactagggac tccttacgaa    1680
cgttgcgctc cgctggaagc catggcaaat cgatgcgtct ttctcaaacc gaagttcccc    1740
ccacccaatt caaggaagaa tacagagttt ttacgaggca gcccacctc cagagaggtg    1800 ttctcccagc atccctacgc ggagaacttc atcggcaagc ccacgtgtg acagtcgac    1860 tacaacaact cagaggagtt tgaagcagcc atcaaggcca ttatgagaac tcaggtagac    1920
ccctacctac cctacgagta cacctgcgag gggatgctgg agcggatcac cgcctacatc    1980
cagcaccagg acttctgcag agcttcagaa cactgccacc cacccagttt tataatccgc    2040
tccctctcca gggcaacccc acctttccca ttccagggta acccgactac acggctaaga    2100
cttgttctac cgccgtttcc agaactagcc gggccttgta gtcaccggaa ccaccccggg    2160
ggtaaaaaat tatattggtt ttctcgtact aatttatggg gtgaatctaa tcgtgatact    2220 ttattttat ctttttttaa agattttattt ttagaaatta ttaaatattt ttattgggat    2280
gttcgttgtc gtcgttaa                                                   2298
```

<210> SEQ ID NO 10
<211> LENGTH: 765
<212> TYPE: PRT
<213> ORGANISM: Homo sapiens

<400> SEQUENCE: 10

```
Met Phe Phe Thr Ile Ser Arg Lys Asn Met Ser Gln Lys Leu Ser Leu
 1               5                  10                  15

Leu Leu Leu Val Phe Gly Leu Ile Trp Gly Leu Met Leu Leu His Tyr
            20                  25                  30

Thr Phe Gln Gln Pro Arg His Gln Ser Ser Val Lys Leu Arg Glu Gln
        35                  40                  45

Ile Leu Asp Leu Ser Lys Arg Tyr Val Lys Ala Leu Ala Glu Glu Asn
    50                  55                  60

Lys Asn Thr Val Asp Val Glu Asn Gly Ala Ser Met Ala Gly Tyr Ala
65                  70                  75                  80

Asp Leu Lys Arg Thr Ile Ala Val Leu Leu Asp Asp Ile Leu Gln Arg
```

-continued

```
                  85                  90                  95
Leu Val Lys Leu Glu Asn Lys Val Asp Tyr Ile Val Val Asn Gly Ser
            100                 105                 110
Ala Ala Asn Thr Thr Asn Gly Thr Ser Gly Asn Leu Val Pro Val Thr
            115                 120                 125
Thr Asn Lys Arg Thr Asn Val Ser Gly Ser Ile Arg Ile Ala Val Glu
            130                 135                 140
Asn His Leu Val Leu Leu His Pro Leu Trp Ile Ile Ser Tyr Gly Arg
145                 150                 155                 160
Lys Ala Leu Tyr Cys Trp Leu Arg Thr Glu Ala Ile Leu Tyr Asn Lys
                165                 170                 175
Ser Thr Asn Gly Gly Gln Asp Lys Cys Val Phe Pro Pro Ile Asp Gly
            180                 185                 190
Tyr Pro His Tyr Glu Gly Lys Ile Lys Trp Ile Asn Asp Met Cys Arg
            195                 200                 205
Ser Asp Pro Cys Lys Ala His Tyr Gly Ile Asp Gly Ser Ser Cys Thr
            210                 215                 220
Phe Phe Ile Tyr Leu Ser Asp Ala Asp Asn His Cys Pro His Ala Pro
225                 230                 235                 240
Trp Arg His Lys Asn Pro Tyr Asp Asp Ala Glu His Asn Ser Cys Ala
                245                 250                 255
Glu Ile Arg Ser Asp Phe Glu Leu Leu Tyr Ser Val Ile His His Lys
                260                 265                 270
Asp Glu Phe His Phe Met Arg Leu Arg Arg Arg Met Val Glu Gly
            275                 280                 285
Trp Ala Gln Ile Ala Lys Ser Leu Ala Asp Lys Gln Asn Ala Glu Lys
            290                 295                 300
Lys Lys Arg Lys Lys Ala Leu Val His Leu Gly Ile Ile Thr Lys Asp
305                 310                 315                 320
Thr Val Ser Lys Ile Ala Glu Thr Gly Phe Ser Ala Ala Pro Leu Gly
                325                 330                 335
Asp Leu Val His Trp Ser Asp Val Ile Thr Ser Ala Tyr Ala Ala Gly
            340                 345                 350
His Asp Val Arg Ile Thr Ala Ser Leu Ala Glu Leu Lys Asp Val Val
            355                 360                 365
Lys Lys Ile Ile Gly Asn Arg Ser Gly Cys Pro Ser Val Gly Asp Arg
            370                 375                 380
Ile Val Glu Leu Leu Tyr Ala Asp Val Ile Gly Leu Gly Gln Phe Lys
385                 390                 395                 400
Lys Thr Leu Gly Pro Thr Trp Ala Gln His Arg Trp Met Val Arg Val
                405                 410                 415
Leu Glu Thr Phe Gly Ser Asp Pro Asp Phe Glu His Ala Asn Tyr Ala
            420                 425                 430
Gln Thr Lys Gly His Lys Ser Pro Trp Gly Trp Asn Leu Asn Pro
            435                 440                 445
Asn Asn Phe Tyr Thr Met Phe Pro His Thr Pro Glu Asn Thr Phe Leu
450                 455                 460
Gly Phe Ala Ile Glu Gln His Leu Asn Ser Ser Asp Met His His Leu
465                 470                 475                 480
Asn Glu Met Lys Arg Gln Asn Gln Thr Leu Val Tyr Gly Lys Val Asp
                485                 490                 495
Ser Phe Trp Lys Asn Lys His Ile Tyr Phe Glu Ile Ile His Asn Tyr
            500                 505                 510
```

-continued

Ile Glu Val Gln Ala Thr Val Tyr Asp Ser Ser Thr Pro Asn Ile Pro
        515                 520                 525
Ser Tyr Ser Arg Asn His Gly Ile Leu Ser Gly Arg Asp His Arg Phe
    530                 535                 540
Leu Leu Arg Glu Thr Phe Leu Leu Leu Gly Leu Gly Thr Pro Tyr Glu
545                 550                 555                 560
Arg Cys Ala Pro Leu Glu Ala Met Ala Asn Arg Cys Val Phe Leu Lys
                565                 570                 575
Pro Lys Phe Pro Pro Asn Ser Arg Lys Asn Thr Glu Phe Leu Arg
            580                 585                 590
Gly Lys Pro Thr Ser Arg Glu Val Phe Ser Gln His Pro Tyr Ala Glu
        595                 600                 605
Asn Phe Ile Gly Lys Pro His Val Trp Thr Val Asp Tyr Asn Asn Ser
    610                 615                 620
Glu Glu Phe Glu Ala Ala Ile Lys Ala Ile Met Arg Thr Gln Val Asp
625                 630                 635                 640
Pro Tyr Leu Pro Tyr Glu Tyr Thr Cys Glu Gly Met Leu Glu Arg Ile
                645                 650                 655
Thr Ala Tyr Ile Gln His Gln Asp Phe Cys Arg Ala Ser Glu His Cys
            660                 665                 670
His Pro Pro Ser Phe Ile Ile Arg Ser Leu Ser Arg Ala Thr Pro Pro
        675                 680                 685
Phe Pro Phe Gln Gly Asn Pro Thr Thr Arg Leu Arg Leu Val Leu Pro
    690                 695                 700
Pro Phe Pro Glu Leu Ala Gly Pro Cys Ser His Arg Asn His Pro Gly
705                 710                 715                 720
Gly Lys Lys Leu Tyr Trp Phe Ser Arg Thr Asn Leu Trp Gly Glu Ser
                725                 730                 735
Asn Arg Asp Thr Leu Phe Leu Ser Phe Phe Lys Asp Leu Phe Leu Glu
            740                 745                 750
Ile Ile Lys Tyr Phe Tyr Trp Asp Val Arg Cys Arg Arg
        755                 760                 765

<210> SEQ ID NO 11
<211> LENGTH: 237
<212> TYPE: DNA
<213> ORGANISM: Homo sapiens

<400> SEQUENCE: 11
cctttcccat tccagggtaa cccgactaca cggctaagac ttgttctacc gccgtttcca      60
gaactagccg ggccttgtag tcaccggaac cacccegggg gtaaaaaatt atattggttt     120
tctcgtacta atttatgggg tgaatctaat cgtgatactt tatttttatc tttttttaaa    180
gatttatttt tagaaattat taaatatttt tattgggatg ttcgttgtcg tcgttaa       237

<210> SEQ ID NO 12
<211> LENGTH: 78
<212> TYPE: PRT
<213> ORGANISM: Homo sapiens

<400> SEQUENCE: 12

Pro Phe Pro Phe Gln Gly Asn Pro Thr Thr Arg Leu Arg Leu Val Leu
 1               5                  10                  15
Pro Pro Phe Pro Glu Leu Ala Gly Pro Cys Ser His Arg Asn His Pro
            20                  25                  30

```
Gly Gly Lys Lys Leu Tyr Trp Phe Ser Arg Thr Asn Leu Trp Gly Glu
         35                  40                  45

Ser Asn Arg Asp Thr Leu Phe Leu Ser Phe Phe Lys Asp Leu Phe Leu
     50                  55                  60

Glu Ile Ile Lys Tyr Phe Tyr Trp Asp Val Arg Cys Arg Arg
 65                  70                  75

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 13
cagacctggt cggcccctgc agccacag                                           28

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 14
ggaggcagcc ccgggagctg ggag                                               24

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 15
ggtcaagata aatgcgtttt tccaccgatc                                         30

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 16
gtggattata tcctatggca gaaaagcttt atat                                    34
```